US012594030B1

(12) United States Patent     (10) Patent No.:   US 12,594,030 B1

Smith et al.     (45) Date of Patent:     Apr. 7, 2026

(54) REGIONAL BODY COMPOSITION FROM TWO-DIMENSIONAL COLOR BODY IMAGES

(71) Applicant: Amazon Technologies, Inc., Seattle, WA (US)

(72) Inventors: Brandon Michael Smith, Fremont, CA (US); Siddhartha Chandra, Santa Cruz, CA (US); Durga Venkata Kiran Yakkala, Eluru (IN); Ganesh Subramanian Iyer, Sunnyvale, CA (US); Siddharth Choudhary, San Jose, CA (US); JinJin Li, San Jose, CA (US); Prakash Ramu, Beaverton, OR (US); Antonio Criminisi, Cambridge (GB); Steven Heymsfield, Baton Rouge, LA (US)

(73) Assignee: Amazon Technologies, Inc., Seattle, WA (US)

( * ) Notice: Subject to any disclaimer, the term of this patent is extended or adjusted under 35 U.S.C. 154(b) by 697 days.

(21) Appl. No.: 17/933,048

(22) Filed: Sep. 16, 2022

(51) Int. Cl.
    *G06T 15/00*       (2011.01)
    *A61B 5/00*       (2006.01)

(52) U.S. Cl.
    CPC .......... *A61B 5/4872* (2013.01); *A61B 5/7275* (2013.01); *G06T 15/005* (2013.01)

(58) Field of Classification Search
    CPC . G06T 7/62; G06T 7/0014; G06T 7/11; G06T 17/00; G06T 2207/20084; G06T 2207/30196; G06V 40/103
    See application file for complete search history.

(56) References Cited

U.S. PATENT DOCUMENTS

| | | | |
|---|---|---|---|
| 6,188,925 | B1 | 2/2001 | Kawanishi et al. |
| 6,468,209 | B1 | 10/2002 | Heymsfield et al. |
| 8,918,162 | B2 | 12/2014 | Prokoski |
| 8,982,147 | B2 | 3/2015 | Ramani et al. |
| 9,801,550 | B2 | 10/2017 | Ferrantelli |

(Continued)

FOREIGN PATENT DOCUMENTS

| | | |
|---|---|---|
| CA | 2884668 A1 | 9/2016 |
| CN | 106295205 A | 1/2017 |

(Continued)

OTHER PUBLICATIONS

Anguelov, D., Srinivasan, P., Koller, D., Thrun, S., Rodgers, J. and Davis, J., "Scape: Shape Completion and Animation of People," ACM Trans. Graph. (Proc. SIGGRAPH), 24(3):408-416, Jul. 2005, 9 pages, http://robots.stanford.edu/papers/anguelov.shapecomp.pdf.

(Continued)

*Primary Examiner* — Jitesh Patel

(74) *Attorney, Agent, or Firm* — Athorus, PLLC

(57) ABSTRACT

Described are systems and methods to determine one or more regional body composition values for one or more regions of a body based on a processing of one or more two-dimensional images that include a representation of the body. Regional body composition values may include any of a fat tissue mass, a lean muscle mass, a bone mineral density, a skeletal muscle mass, etc., which may be determined for any one or more regions of the body, such as the right arm, left arm, right leg, left leg, trunk, android, gynoid, etc.

20 Claims, 20 Drawing Sheets

(5) PROCESS USER INFORMATION AND 2D COLOR BODY DIRECTION IMAGE(S) TO GENERATE PERSONALIZED 3D BODY PARAMETERS AND REGIONAL BODY COMPOSITION (3) SEND USER INFORMATION
(4) SEND 2D COLOR BODY DIRECTION IMAGE(S)

(1) OBTAIN USER INFORMATION
(2) OBTAIN 2D COLOR BODY IMAGE(S) OF USER FROM ONE OR MORE BODY DIRECTIONS

COMPUTING RESOURCE(S) 103

3D BODY MODEL SYSTEM 101

100
125
130

(6) SEND PERSONALIZED 3D BODY PARAMETERS AND REGIONAL BODY COMPOSITION
(7) RENDER PERSONALIZED 3D BODY MODEL
(8) PRESENT PERSONALIZED 3D BODY MODEL, AND REGIONAL BODY COMPOSITION
(9) ENABLE INTERACTION WITH PERSONALIZED 3D BODY MODEL

(56)    References Cited

U.S. PATENT DOCUMENTS

| | | | |
|---|---|---|---|
| 9,839,376 | B1 | 12/2017 | Ross et al. |
| 10,321,728 | B1 | 6/2019 | Koh et al. |
| 10,489,683 | B1 | 11/2019 | Koh et al. |
| 10,559,111 | B2 | 2/2020 | Sachs et al. |
| 10,636,158 | B1 | 4/2020 | Kamiyama et al. |
| 10,657,709 | B2 | 5/2020 | Moore et al. |
| 10,748,217 | B1 | 8/2020 | Ross et al. |
| 10,789,725 | B2 | 9/2020 | Segman |
| 10,796,480 | B2 | 10/2020 | Chen et al. |
| 10,926,404 | B2 | 2/2021 | Jackson et al. |
| 10,945,813 | B2 | 3/2021 | Li et al. |
| 11,069,131 | B2 | 7/2021 | Agrawal et al. |
| 11,232,629 | B1 | 1/2022 | Seymore et al. |
| 11,423,630 | B1 | 8/2022 | Agrawal et al. |
| 11,507,203 | B1 | 11/2022 | Bosworth |
| 2004/0151366 | A1 | 8/2004 | Nefian et al. |
| 2005/0251347 | A1 | 11/2005 | Perona et al. |
| 2006/0061583 | A1 | 3/2006 | Spooner et al. |
| 2006/0222206 | A1 | 10/2006 | Garoutte |
| 2012/0139925 | A1 | 6/2012 | Wang et al. |
| 2012/0190505 | A1 | 7/2012 | Shavit et al. |
| 2013/0325493 | A1 | 12/2013 | Wong et al. |
| 2014/0121564 | A1 | 5/2014 | Raskin |
| 2014/0267611 | A1 | 9/2014 | Kennett et al. |
| 2014/0340479 | A1 | 11/2014 | Moore et al. |
| 2015/0154453 | A1 | 6/2015 | Wilf |
| 2015/0227652 | A1 | 8/2015 | Aonuma |
| 2016/0089573 | A1 | 3/2016 | House et al. |
| 2016/0203361 | A1* | 7/2016 | Black ..................... G06T 7/75 |
| | | | 382/203 |
| 2016/0247017 | A1 | 8/2016 | Sareen et al. |
| 2016/0284123 | A1 | 9/2016 | Hare et al. |
| 2017/0273639 | A1 | 9/2017 | Iscoe et al. |
| 2017/0368413 | A1 | 12/2017 | Shavit |
| 2018/0089821 | A1 | 3/2018 | Koldyshev |
| 2018/0289334 | A1 | 10/2018 | Brouwer et al. |
| 2018/0330810 | A1 | 11/2018 | Gamarnik et al. |
| 2019/0122424 | A1 | 4/2019 | Moore et al. |
| 2019/0191137 | A1 | 6/2019 | Bisti |
| 2019/0347817 | A1 | 11/2019 | Ferrantelli et al. |
| 2019/0362546 | A1* | 11/2019 | Wayenberg ............. G06T 19/20 |
| 2020/0193710 | A1 | 6/2020 | Talgorn et al. |
| 2020/0319015 | A1 | 10/2020 | Kamiyama et al. |
| 2021/0001172 | A1 | 1/2021 | Namboodiri |
| 2021/0097759 | A1* | 4/2021 | Agrawal ................. G06T 19/20 |
| 2021/0232924 | A1 | 7/2021 | Sun et al. |
| 2021/0235802 | A1* | 8/2021 | Koh ........................ G06T 11/00 |
| 2021/0241522 | A1 | 8/2021 | Guler et al. |
| 2022/0072377 | A1 | 3/2022 | Russell et al. |
| 2022/0147735 | A1 | 5/2022 | Suh et al. |
| 2022/0292351 | A1 | 9/2022 | Etemad et al. |
| 2023/0065288 | A1 | 3/2023 | Valsan et al. |

FOREIGN PATENT DOCUMENTS

| | | |
|---|---|---|
| CN | 108652584 A | 10/2018 |
| CN | 110051353 A | 7/2019 |
| WO | 2022204343 A1 | 9/2022 |

OTHER PUBLICATIONS

Anonymous: "BMI 3D", www.bmi3d.de; Nov. 25, 2018 (Nov. 25, 2018), XP002801424, URL: https://web.archive.org/web/20181125231845/https://www.bmi3d.de/rechner.html [Retrieved from the Internet on Dec. 16, 2020]; the whole document.

Anonymous: "Documentation: What is MakeHuman?", MakeHuman, May 20, 2016 (May 20, 2016), XP002801426, URL: http://www.makehumancommunity.org/wiki/Documentation:What is MakeHuman%3F [Retrieved from the Internet on Jan 30, 2021]; the whole document.

Anonymous: "Virtual Weight Loss Simulator", www.changeinseconds.com; Dec. 11, 2016 (Dec. 11, 2016), XP002801425, URL: https://web.archive.org/web/20161206202928;%20/http://www.

changeinseconds.com/simulator/ [Retrieved from the Internet on Dec. 16, 2020]; the whole document.

Bălan, A. O. and Black, M. J., "The Naked Truth: Estimating Body Shape under Clothing," In European Conference on Computer Vision (ECCV), 2008, 15 pages, https://www.researchgate.net/profile/Michael_Black6/publication/221305001_The_Naked_Truth_Estimating_Body_Shape_Under_Clothing/links/0fcfd512d21f538458000000/The-Naked-Truth-Estimating-Body-Shape-Under-Clothing.pdf?origin=publication_detail.

Bălan, A. O., Sigal, L., Black, M. J., Davis, J. E. and Haussecker, H. W., "Detailed Human Shape and Pose from Images," In IEEE Conference on Computer Vision and Pattern Recognition (CVPR), 2007, 9 pages.

Biggs, Benjamin, et al. "3D Multi-bodies: Fitting Sets of Plausible 3D Human Models to Ambiguous Image Data." Advances in Neural Information Processing Systems 34 (2020): 20496-20507. (Year: 2020).

Bogo, F., Kanazawa, A., Lassner, C., Gehler, P., Romero, J. and Black, M. J., "Keep it SMPL: Automatic Estimation of 3D Human Pose and Shape from a Single Image," In European Conference on Computer Vision (ECCV), 2016, 21 pages, https://arxiv.org/pdf/1607.08128v1.pdf.

Boisvert, J., Shu, C., Wuhrer, S., and Xi, P., "Three-Dimensional Human Shape Inference from Silhouettes: Reconstruction and Validation," Machine Vision and Applications, 24(1):145-157, 2013, 13 pages, http://people.scs.carleton.ca/~c_shu/Publications/silhouettes_human_rec_MVA11.pdf.

Bukar et al., "Automatic age and gender classification using supervised appearance model," Journal of Electronic Imaging, Aug. 2016; 25(6):0601605, 12 pages.

Chen, W., Wang, H., Li, Y., Su, H., Wang, Z., Tu, C., Lischinski, D., Cohen-Or, D. and Chen, B. Synthesizing Training Images for Boosting Human 3D Pose Estimation. In 2016 Fourth International Conference on 3D Vision (3DV) Oct. 2, 20165 (pp. 479-488). IEEE, 10 pages.

Chen, X., Guo, Y., Zhou, B. and Zhao, Q., "Deformable Model for Estimating Clothing and Naked Human Shapes from a Single Image," The Visual Computer, 29(11):1187-1196, 2013, 10 pages.

Chen, Y., Kim, T.-K. and Cipolla, R., "Inferring 3D Shapes and Deformations from Single Views," In European Conference on Computer Vision, 2010, 14 pages.

Chen, Y., Kim, T.-K. and Cipolla, R., Silhouette-Based Object Phenotype Recognition Using 3D Shape Priors. In Inter-national Conference on Computer Vision (ICCV), 2011, 8 pages.

Devries, T. and Taylor, G. W., Learning Confidence for Out-of-Distribution Detection in Neural Networks, arXiv preprint arXiv:1802.04865, 2018, 12 pages.

Dibra Endri et al: "HS-Nets: Estimating Human Body Shape from Silhouettes with Convolutional Neural Networks", 2016 Fourth International Conference on 30 Vision (30V), IEEE, Oct. 25, 2016 (Oct. 25, 2016), pp. 108-117, XP033027616, DOI: 10.1109/3DV.2016.19 [retrieved on Dec. 15, 2016].

Dibra, E., Jain, H., Öztireli, C., Ziegler, R. and Gross, M., "HSNets: Estimating Human Body Shape from Silhouettes with Convolutional Neural Networks," In International Conference on 3D Vision (3DV), 2016, 10 pages.

Dibra, E., Jain, H., Öztireli, C., Ziegler, R. and Gross, M., "Human Shape from Silhouettes Using Generative HKS Descriptors and Cross-Modal Neural Networks," In IEEE Conference on Computer Vision and Pattern Recognition (CVPR), 2017, 11 pages.

Dibra, E., Jain, H., Öztireli, C., Ziegler, R. and Gross, M., "Shape from Selfies: Human Body Shape Estimation Using CCA Regression Forests," In European Converence on Computer Vision (ECCV), 2016, 17 pages.

Dibra, Endri: "Recovery of the 3D Virtual Human: Monocular Estimation of 3D Shape and Pose with Data Driven Priors", May 31, 2018 (May 31, 2018), pp. 1-192, XP055648769, DOI: 10.3929/ethz-b-000266852 Retrieved from the Internet: URL: https://www.research-collection.ethz.ch/bitstream/handle/20.500.11850/266852/Endri_Dibra_Thesis_Final.pdf?sequence=3&isAllowed=y [retrieved on Dec. 3, 2019].

(56)                    References Cited

OTHER PUBLICATIONS

Gilbert, A., Volino, M., Collomosse, J. and Hilton, A.,"Volumetric Performance Capture from Minimal Camera View-Points," In European Conference on Computer Vision, 2018, 16 pages.

Gong, K., Liang, X., Zhang, D., Shen, X. and Lin, L., "Look into Person: Self-Supervised Structure-Sensitive Learning and a New Benchmark for Human Parsing," In IEEE Conference on Computer Vision and Pattern Recognition (CVPR), 2017, 9 pages.

Grinciunaite, A., et al., "Human Pose Estimation in Space and Time Using 3D CNN," ECCV Workshop on Brave New Ideas for Motion Representations in Videos, Oct. 19, 2016, URL: https://arxiv.org/pdf/1609.00036.pdf, 7 pages.

Guan, P., Weiss, A., Bălan, A. O. and Black, M. J., "Estimating Human Shape and Pose from a Single Image," In IEEE International Conference on Computer Vision (ICCV), 2009, 8 pages.

Güler, R. A., Neverova, N. and Kokkinos, I., "DensePose: Dense Human Pose Estimation in the Wild," In IEEE Conference on Computer Vision and Pattern Recognition (CVPR), 2018, 10 pages.

Harville, M., "Stereo Person Tracking with Adaptive Plan-View Templates of Height and Occupancy Statistics," Image and Vision Computing, vol. 22, Issue 2, Feb. 1, 2004, https://www.researchgate.net/publication/223214495_Stereo_person_tracking_with_adaptive_plan-view_templates_of_height_and_occupancy_statistics/link/5e294888a6fdcc70a1437262/download, pp. 127-142.

Hassan B, Izquierdo E and Piatrik T. Soft Biometrics: A Survey Benchmark Analysis, Open Challenges and Recommendations. Multimedia Tools and Applications. Mar. 2, 2021, 44 pages.

He, K., Zhang, X., Ren, S. and Sun, J., "Deep Residual Learning for Image Recognition," In IEEE Conference on Computer Vision and Pattern Recognition (CVPR), 2016, 10 pages.

Hirano, D., Funayama, Y. and Maekawa, T. 3D Shape Reconstruction From 2D Images. Computer-Aided Design and Applications. 2009 CAD Solutions, LLC. Jan. 1, 2009 ;6(5):701-10, 10 pages.

Horprasert, T., Harwood, D. and Davis, L. S., "A Statistical Approach for Real-Time Robust Background Subtraction and Shadow Detection," In IEEE International Conference on Computer Vision (ICCV), 1999, 19 pages.

Huang Z, Barrett JS, Barrett K, Barrett R, Ng CM. Novel method to predict body weight in children based on age and morphological facial features. The Journal of Clinical Pharmacology. Apr. 2015;55(4):447-51.

Ji, Z., et al.; "Human Body Shape Reconstruction from Binary Silhouette Images;" Computer Aided Geometric Design 71 (2019) pp. 231-243; Elsevier B.V. (Year: 2019).

Joo, H., Simon, T. and Y. Sheikh, Y., "Total Capture: A 3D Deformation Model for Tracking Faces, Hands, and Bodies," In IEEE Conference on Computer Vision and Pattern Recognition (CVPR), 2018, 10 pages.

Kanazawa, A., Black, M. J., Jacobs, D. W. and Malik, J., "End-to-End Recovery of Human Shape and Pose," In IEEE Conference on Computer Vision and Pattern Recognition (CVPR), 2018, 10 pages.

Kocabey E, Camurcu M, Ofli F, Aytar Y, Marin J, Torralba A, Weber I. Face-to-BMI: Using computer vision to infer body mass index on social media. In Proceedings of the International AAAI Conference on Web and Social Media May 3, 2017 (vol. 11, No. 1, pp. 572-575).

Kolotouros, N. et al. "Learning to Reconstruct 3D Human Pose and Shape via Model-fitting in the Loop," In Proceedings of the IEEE International Conference on Computer Vision, 2019, Sep. 27, 2019, URL: https://arxiv.org/abs/1909.12828, 10 pages.

Krasin, I., Duerig, T., Alldrin, N., Ferrari, V., Abu-El-Haija, S., Kuznetsova, A., Rom, H., Uijlings, J., Popov, S., Kamali, S., Malloci, M., Pont-Tuset, J., Veit, A., Belongie, S., Gomes, V., Gupta, A., Sun, C., Chechik, G., Cai, D., Feng, Z., Narayanan, D., and Murphy, K., "Openimages: A Public Dataset for Large-Scale Multi-Label and Multi-Class Image Classification," Dataset available from https://storage.googleapis.com/openimages/web/index.html, 2017.

Kundu, A., Li, Y. and Rehg, J. M., "3D-RCNN: Instance-Level 3D Object Reconstruction via Render-and-Compare," In IEEE Conference on Computer Vision and Pattern Recognition (CVPR), 2018, 10 pages.

Lassner, C., Romero, J., Kiefel, M., Bogo, F., Black, M. J. and Gehler, P. V., "Unite the People—Closing the Loop Between 3D and 2D Human Representations," In IEEE Conference on Computer Vision and Pattern Recognition (CVPR), 2017, 10 pages.

Lee BJ, Jang JS, Kim JY. Prediction of body mass index from facial features of females and males. International Journal of Bio-Science and Bio-Technology. Sep. 2012;4(3):45-62.

Lee BJ, Kim JY. Predicting visceral obesity based on facial characteristics. BMC Complementary and Alternative Medicine. Dec. 2014;14(1):1-9.

Li, K., R. Garg, M. Cai and I. Reid, "Single-view Object Shape Reconstruction Using Deep Shape Prior and Silhouette," The School of Computer Science, University of Adelaide and Australian Centre for Robotic Vision. Adelaide, Australia, arXiv preprint arXiv: 1811.11921. Aug. 1, 2019, Cornell University, URL: https://arxiv.org/pdf/1811.11921.pdf, 14 pages.

Long, J., Shelhamer, E., and Darrell, T., "Fully Convolutional Networks for Semantic Segmentation,"In IEEE Conference on Computer Vision and Pattern Recognition (CVPR), 2015, 10 pages.

Longuet-Higgins, H.C., "A Computer Algorithm for Reconstructing a Scene from Two Projections," Nature 293, Sep. 10, 1981, https://cseweb.ucsd.edu/classes/fa01/cse291/hclh/SceneReconstruction.pdf, pp. 133-135.

Loper, M., Mahmood, N., Romero, J., Pons-Moll, G. and Black, M. J., "SMPL: A Skinned Multi-Person Linear Model," ACM Trans. Graphics (Proc. SIGGRAPH Asia), 34(6):248:1-248:16, Oct. 2015, 16 pages.

Mülayim, A. Y., Yilmaz, U. and Atalay, V. Silhouette-based 3D Model Reconstruction from Multiple Images. IEEE Transactions on Systems, Man, and Cybernetics, Part B (Cybernetics). Jul. 22, 2003;33(4):582-91, 27 pages.

nakedlabs.com, Aug. 2, 2018 (Aug. 2, 2018), XP002801423, URL: https://web.archive.org/web/20180802014000/https://nakedlabs.com/ [Retrieved from the Internet: Dec. 16, 2020]; the whole document.

Nambiar A, Bernardino A and Nascimento J. Shape Context for Soft Biometrics in Person Re-Identification and Database Retrieval. Pattern Recognition Letters. Dec. 15, 2015; 68:297-305.

Ngiam, J., Khosla, A., Kim, M., Nam, J., Lee, H. and NG, A. Y., "Multimodal Deep Learning," In International Conference on Machine Learning (ICML), pp. 689-696, 2011, 8 pages.

Nguyen et al., "Gender Recognition from Human-Body Images Using Visible-Light and Thermal Camera Videos Based on a Convolutional Neural Network for Image Feature Extraction," Sensors,Mar. 2017: 17(3);637, 22 pages.

Omran, M., Lassner, C., Pons-Moll, G., Gehler, P. V. and Schiele, B., "Neural Body Fitting: Unifying Deep Learning and Model-Based Human Pose and Shape Estimation," In International Conference on 3D Vision (3DV), 2018, 14 pages.

Park, S., Hwang, J. and Kwak, N. 3D Human Pose Estimation Using Convolutional Neural Networks with 2D Pose Information. In European Conference on Computer Vision, Sep. 8, 2016 (pp. 156-169), https://arxiv.org/pdf/1608.03075v2.pdf, 15 pages.

Pavlakos et al., "Expressive Body Capture: 3D Hands, Face, and Body from a Single Image," 2019 IEEE/CVF Conference on Computer Vision and Pattern Recognition (CVPR), Jun. 1, 2019, 11 pages.

Pavlakos, G., Zhu, L., Zhou, X. and Daniilidis, K., "Learning to Estimate 3D Human Pose and Shape from a Single Color Image," In IEEE Conference on Computer Vision and Pattern Recognition (CVPR), 2018, 10 pages.

Popa, A.-I., Zanfir, M. and C. Sminchisescu, C., "Deep Multitask Architecture for Integrated 2D and 3D Human Sensing," In IEEE Conference on Computer Vision and Pattern Recognition (CVPR), 2017, 10 pages.

Pradhan, L., et al., Feature Extraction from 2D Images for Body Composition Analysis, 2015 IEEE 978-1-5090-0379-2/15, DOI 10.1109/ ISM.2015.117, pp. 45-52. (Year: 2015).

(56)          References Cited

OTHER PUBLICATIONS

Ramanathan V and Wechsler H. Robust Human Authentication Using Appearance and Holistic Anthropometric Features. Pattern Recognition Letters. Nov. 1, 2010; 31(15):2425-35.

Rhodin, H., Robertini, N., Casas, D., Richardt, C., Seidel, H.-P. and Theobalt, C., "General Automatic Human Shape and Motion Capture Using Volumetric Contour Cues," In European Conference on Computer Vision, 2016, 18 pages.

Robinette, K. M., Blackwell, S., Daanen, H., Boehmer, M., Fleming, S., Brill, T., Hoeferlin, D. and Burnsides, D., "Civilian American and European Surface Anthropometry Resource (CAESAR) Final Report," Tech. Rep. AFRL-HEWP-TR-2002-0169, US Air Force Research Laboratory, 2002, 70 pages.

Rogez, G., Weinzaepfel, P. and Schmid C. LCR-Net++: Multi-Person 2D and 3D Pose Detection in Natural Images. IEEE IEEE Transactions on Pattern Analysis and Machine Intelligence, Jan. 14, 2019;42(5): 1146-61, Downloaded on Jul. 18, 2020, 16 pages.

Sengupta, A. et al. "Hierarchical Kinematic Probability Distributions for 3D Human Shape and Pose Estimation from Images in the Wild," In International Conference on Computer Vision, Oct. 2021, URL: https://www.researchgate.net/publication/355060401_Hierarchical_Kinematic_Probability_Distributions_for_3D_Human_Shape_and_Pose_Estimation_from_Images_in_the_Wild, 17 pages.

Sengupta, A. et al. "Synthetic Training for Accurate 3D Human Pose and Shape Estimation in the Wild," In British Machine Vision Conference (BMVC), Sep. 2020, URL: https://www.researchgate.net/publication/344335326_Synthetic_Training_for_Accurate_3D_Human_Pose_and_Shape_Estimation_in_the_Wild, 13 pages.

Seo, Hyewon, Young In Yeo, and Kwangyun Wahn. "3D Body Reconstruction from Photos Based on Range Scan." International Conference on Technologies for E-Learning and Digital Entertainment. Springer-Verlag, Berlin, Heidelberg, 2006. pp. 849-860 (Year: 2006).

Sigal, L., Bălan, A. O. and Black, M. J., "Combined Discriminative and Generative Articulated Pose and Non-Rigid Shape Estimation," In Neural Information Processing Systems (NIPS), 2007, 8 pages.

Smith, Brandon M. et al: "Towards Accurate 3D Human Body Reconstruction from Silhouettes", 2019 International Conference on 3D Vision (3DV), IEEE, Sep. 16, 2019 (Sep. 16, 2019), pp. 279-288 , XP033653362, Doi: 10.1109/3DV. 2019.00039 [retrieved on Oct. 28, 2019].

Su et al., "Multi-view Convolutional Neural Networks for 3D Shape Recognition," 2015 IEEE International Conference on Computer Vision (ICCV), Dec. 7-13, 2015, Santiago, Chile, 9 pages.

Sun, J., Ovsjanikov, M. and Guibas, L., "A Concise and Provably Informative Multi-Scale Signature Based on Heat Diffusion," In Symposium on Geometry Processing, 2009, 10 pages.

Sun, X., Wu, J., Zhang, X., Zhang, Z., Zhang, C., Xue, T., Tenenbaum, J. B. and Freeman, W. T. Pix3D: Dataset and Methods for Single-Image 3D Shape Modeling. In 2018 IEEE/CVF Conference on Computer Vision and Pattern Recognition, Jun. 18, 2018 (pp. 2974-2983). IEEE, 10 pages.

Tan, J. K. V., Budvytis, I. and Cipolla, R., "Indirect Deep Structured Learning for 3D Human Body Shape and Pose Prediction," In British Machine Vision Conference, 2017, 11 pages.

TC2 Labs LLC, "SizeUSA", 3 pages, http://scan2fit.com/sizeusa/about.php.

Tome, D., Russell, C. and Agapito, L. Lifting from the Deep: Convolutional 3D Pose Estimation from a Single Image. In Proceedings of the IEEE Conference on Computer Vision and Pattern Recognition 2017 (pp. 2500-2509), 11 pages.

Varol G, Ceylan D, Russell B, Yang J, Yumer E, Laptev I and Schmid C. Bodynet: Volumetric Inference of 3D Human Body Shapes (and Supplemental Material). In Proceedings of the European Conference on Computer Vision (ECCV) 2018 (pp. 20-36).

Varol, G., Ceylan, D., Russell, B., Yang, J., Yumer, E., Laptev, I. and Schmid, C., "BodyNet: Volumetric Inference of 3D Human Body Shapes," In European Conference on Computer Vision (ECCV), 2018, 17 pages.

Varol, G., Romero, J., Martin, X., Mahmood, N., Black, M. J., Laptev, I. and Schmid, C., "Learning from Synthetic Humans," In IEEE Conference on Computer Vision and Pattern Recognition (CVPR), 2017, 9 pages.

Wiles, Olivia and Andrew Zisserman, "SilNet: Single- and Multi-View Reconstruction by Learning from Silhouettes," Visual Geometry Group, Department of Engineering Science, University of Oxford, Oxford, UK, arXiv preprint arXiv: 1711.07888. Nov. 21, 2017, Cornell University, URL: https://arxiv.org/pdf/1711.07888.pdf, 13 pages.

Xi, P., Lee, W.-S. and Shu, C., "A Data-Driven Approach to Human-Body Cloning Using a Segmented Body Database," In Pacific Conference on Computer Graphics and Applications (PG), 2007, 9 pages.

Xie, H., Yao, H., Sun, X., Zhou, S. and Zhang, S. Pix2Vox: Context-aware 3D Reconstruction from Single and Multi-view Images. arXiv preprint arXiv: 1901.11153, https://arxiv.org/pdf/1901.11153.pdf, Jul. 29, 2019, 9 pages.

Yan, Song et al: "Learning Anthropometry from Rendered Humans", arxiv.org, Cornell University Library, 201 Online Library Cornell University Ithaca, NY, 14853, Jan. 7, 2021 (Jan. 7, 2021), XP081853690.

Yu, F., Zhang, Y., Song, S., Seff, A., and Xiao, J., "LSUN: Construction of a Large-Scale Image Dataset Using Deep Learning with Humans in the Loop," arXiv preprint arXiv:1506.03365, 2015, 9 pages.

Zanfir, A., Marinoiu, E. and Sminchisescu, C., "Monocular 3D Pose and Shape Estimation of Multiple People in Natural Scenes—the Importance of Multiple Scene Constraints," In IEEE Conference on Computer Vision and Pattern Recognition (CVPR), 2018, 10 pages.

Zhang, H., Dana, K., Shi, J., Zhang, Z., Wang, X., Tyagi, A. and Agrawal, A., "Context Encoding for Semantic Segmentation," In the IEEE Conference on Computer Vision and Pattern Recognition (CVPR), Jun. 2018, 10 pages.

Zhang, Tianshu, Buzhen Huang, and Yangang Wang. "Object-Occluded Human Shape and Pose Estimation from a Single Color Image." Proceedings of the I EEE/CVF Conference on Computer Vision and Pattern Recognition. 2020. (Year: 2020) 10 pages.

Zhao, Ruiqi, Yan Wang, and Aleix M. Martinez. "A Simple, Fast and Highly-Accurate Algorithm to Recover 3D Shape from 2D Landmarks on a Single Image." IEEE Transactions on Pattern Analysis and Machine Intelligence, vol. 40, No. 12 (2017): 3059-3066. (Year: 2018).

Zhu, R., H. Kiani Galoogahi, C. Wang and S. Lucey, "Rethinking Reprojection: Closing the Loop for Pose-aware Shape Reconstruction from a Single Image," The Robotics Institute, Carnegie Mellon University, In Proceedings of the IEEE International Conference on Computer Vision, Jul. 26, 2017 (pp. 57-65), 9 pages.

Kato H, Ushiku Y, Harada T. Neural 3D Mesh Renderer. In Proceedings of the IEEE Conference on Computer Vision and Pattern Recognition 2018 (pp. 3907-3916).

Natsume R, Saito S, Huang Z, Chen W, Ma C, Li H, Morishima S. SiCloPe: Silhouette-Based Clothed People. arXiv preprint arXiv: 1901.00049. Dec. 31, 2018.

Song, D., Tong, R., Chang, J., Yang, X., Tang, M., Zhang, J.J. 3D Body Shapes Estimation from Dressed-Human Silhouettes. In Computer Graphics Forum Oct. 2016. (vol. 35, No. 7, pp. 147-156).

* cited by examiner

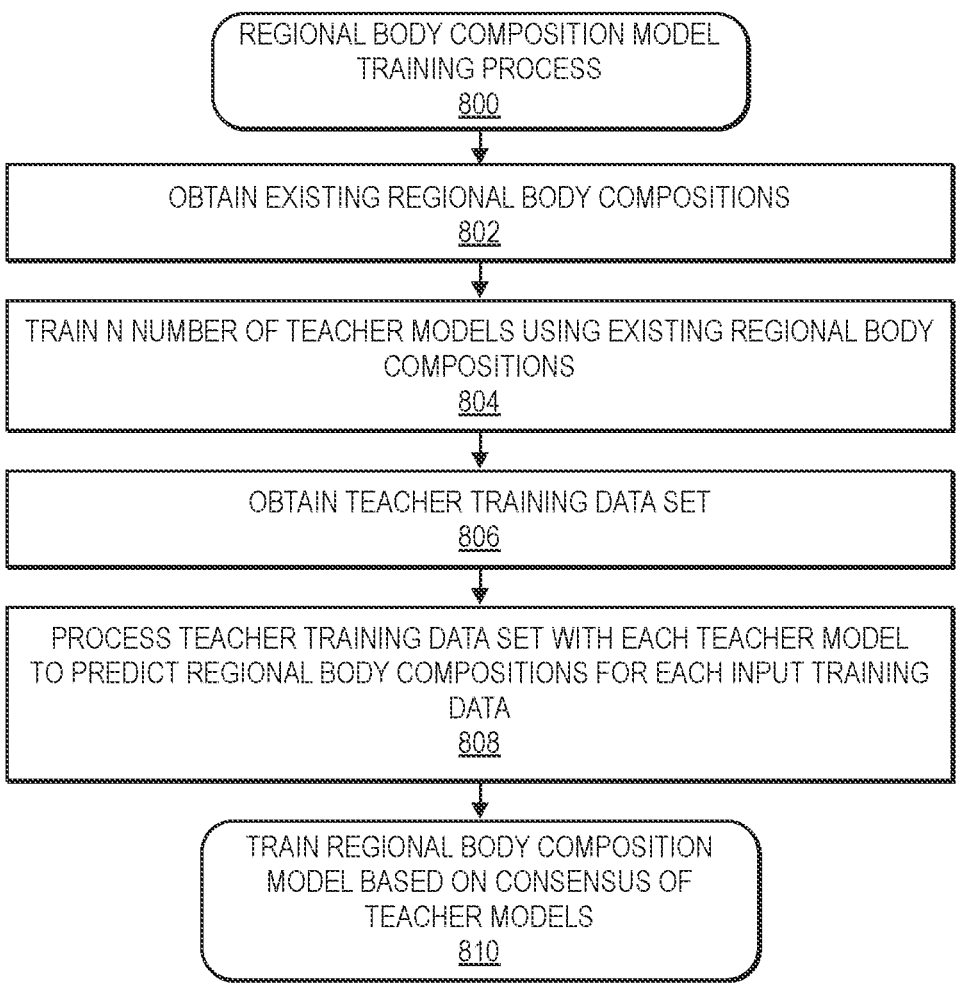

REGIONAL BODY COMPOSITION MODEL
TRAINING PROCESS
800

OBTAIN EXISTING REGIONAL BODY COMPOSITIONS
802

TRAIN N NUMBER OF TEACHER MODELS USING EXISTING REGIONAL BODY
COMPOSITIONS
804

OBTAIN TEACHER TRAINING DATA SET
806

PROCESS TEACHER TRAINING DATA SET WITH EACH TEACHER MODEL
TO PREDICT REGIONAL BODY COMPOSITIONS FOR EACH INPUT TRAINING
DATA
808

TRAIN REGIONAL BODY COMPOSITION
MODEL BASED ON CONSENSUS OF
TEACHER MODELS
810

FIG. 8A

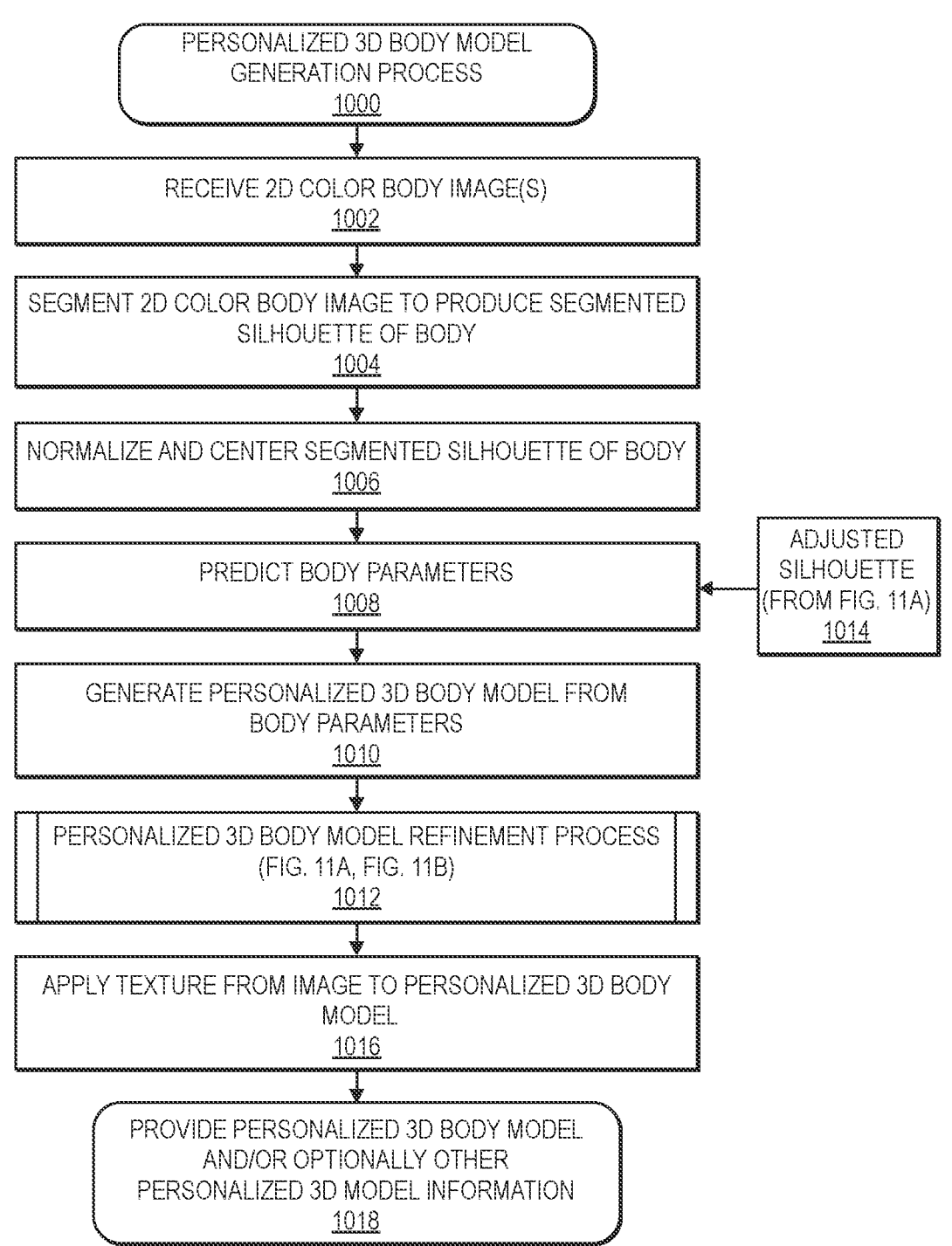

PERSONALIZED 3D BODY MODEL
GENERATION PROCESS
1000

RECEIVE 2D COLOR BODY IMAGE(S)
1002

SEGMENT 2D COLOR BODY IMAGE TO PRODUCE SEGMENTED
SILHOUETTE OF BODY
1004

NORMALIZE AND CENTER SEGMENTED SILHOUETTE OF BODY
1006

PREDICT BODY PARAMETERS
1008

ADJUSTED
SILHOUETTE
(FROM FIG. 11A)
1014

GENERATE PERSONALIZED 3D BODY MODEL FROM
BODY PARAMETERS
1010

PERSONALIZED 3D BODY MODEL REFINEMENT PROCESS
(FIG. 11A, FIG. 11B)
1012

APPLY TEXTURE FROM IMAGE TO PERSONALIZED 3D BODY
MODEL
1016

PROVIDE PERSONALIZED 3D BODY MODEL
AND/OR OPTIONALLY OTHER
PERSONALIZED 3D MODEL INFORMATION
1018

FIG. 10

PERSONALIZED 3D BODY MODEL REFINEMENT
PROCESS
1150

DETERMINE POSE OF BODY IN 2D COLOR BODY IMAGE
1152

ADJUST PERSONALIZED 3D BODY MODEL TO
CORRESPONDING POSE
1154

GENERATE 2D MODEL IMAGE FROM PERSONALIZED 3D
BODY MODEL
1156

DETERMINE DIFFERENCES BETWEEN 2D MODEL IMAGE
AND 2D BODY IMAGE
1158

REFINE PERSONALIZED 3D BODY
PARAMETERS/PERSONALIZED 3D BODY MODEL
1160

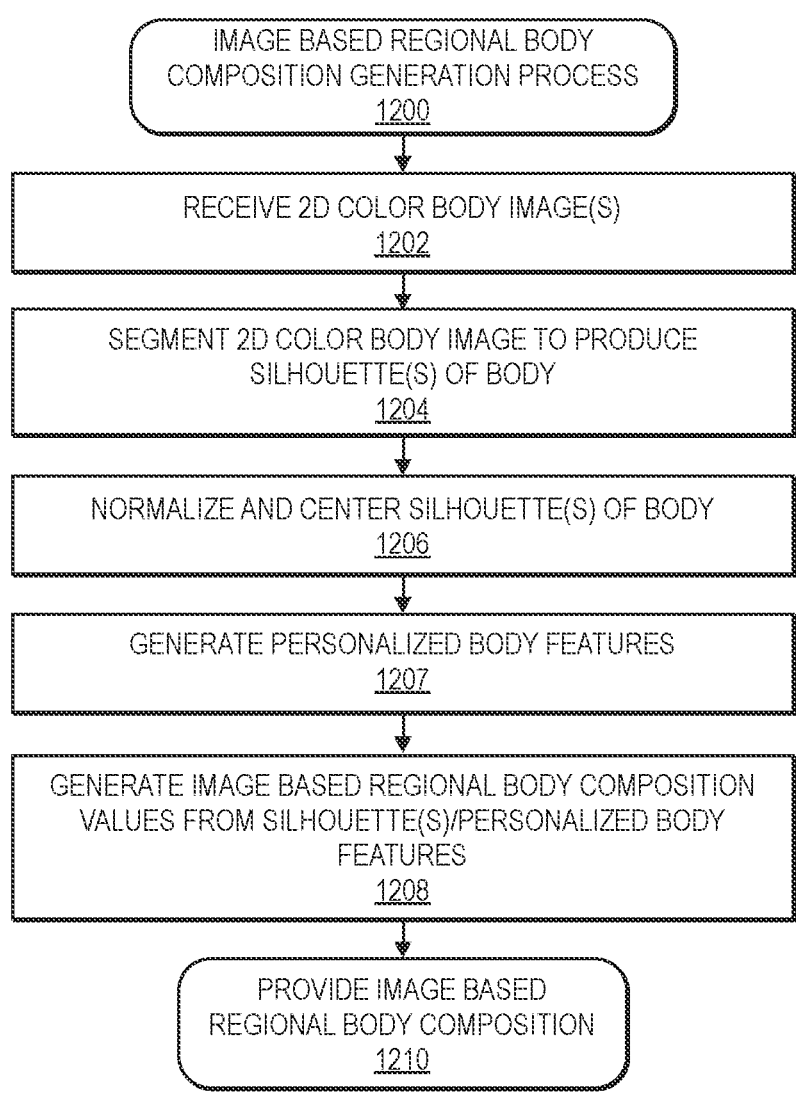

IMAGE BASED REGIONAL BODY
COMPOSITION GENERATION PROCESS
1200

RECEIVE 2D COLOR BODY IMAGE(S)
1202

SEGMENT 2D COLOR BODY IMAGE TO PRODUCE
SILHOUETTE(S) OF BODY
1204

NORMALIZE AND CENTER SILHOUETTE(S) OF BODY
1206

GENERATE PERSONALIZED BODY FEATURES
1207

GENERATE IMAGE BASED REGIONAL BODY COMPOSITION
VALUES FROM SILHOUETTE(S)/PERSONALIZED BODY
FEATURES
1208

PROVIDE IMAGE BASED
REGIONAL BODY COMPOSITION
1210

FIG. 12

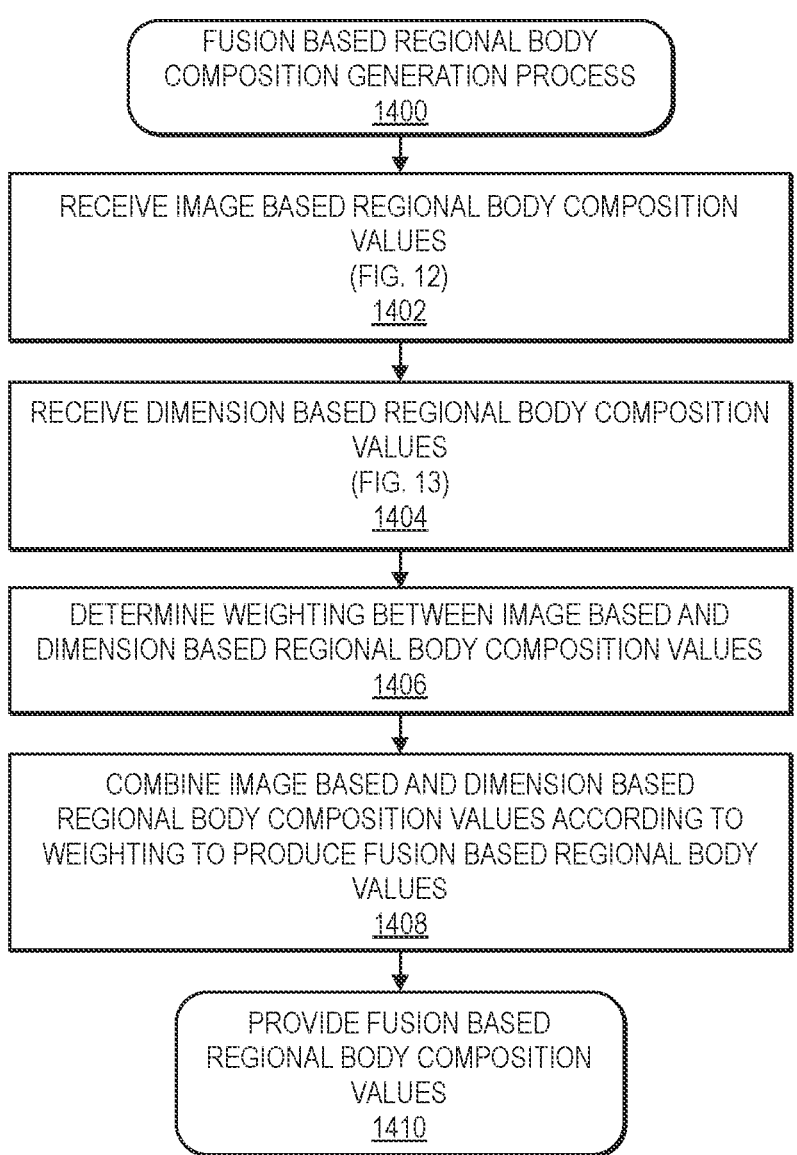

FUSION BASED REGIONAL BODY
COMPOSITION GENERATION PROCESS
1400

RECEIVE IMAGE BASED REGIONAL BODY COMPOSITION
VALUES
(FIG. 12)
1402

RECEIVE DIMENSION BASED REGIONAL BODY COMPOSITION
VALUES
(FIG. 13)
1404

DETERMINE WEIGHTING BETWEEN IMAGE BASED AND
DIMENSION BASED REGIONAL BODY COMPOSITION VALUES
1406

COMBINE IMAGE BASED AND DIMENSION BASED
REGIONAL BODY COMPOSITION VALUES ACCORDING TO
WEIGHTING TO PRODUCE FUSION BASED REGIONAL BODY
VALUES
1408

PROVIDE FUSION BASED
REGIONAL BODY COMPOSITION
VALUES
1410

FIG. 14

REGIONAL BODY COMPOSITION FROM TWO-DIMENSIONAL COLOR BODY IMAGES

BACKGROUND

Existing body fat measurement techniques are either low cost and highly inaccurate, or require large and expensive equipment, along with trained staff, to obtain more accurate results. For example, body calipers and bioelectrical impedance, often found on bathroom scales, are relatively low cost solutions for determining body fat of a body. However, in general, both are highly inaccurate. At the other end of the spectrum are Air Displacement Plethysmograph (ADP) systems that use whole body densitometry to determine body composition (fat vs. lean). Another example includes Dual-energy X-ray absorptiometry (DXA or DEXA) systems that use low-dose X-rays to determine body composition, including body fat. While ADP and DEXA systems are considered highly accurate, they require expensive equipment and trained staff to operate and, in the case of DEXA, may have some negative health related effects due to the use of X-rays.

BRIEF DESCRIPTION OF THE DRAWINGS

FIG. 8A is an example regional body composition model training process, in accordance with implementations of the present disclosure.

FIG. 10 is an example flow diagram of a three-dimensional body model generation process, in accordance with implementations of the present disclosure.

FIG. 12 is an example image based regional body composition generation process, in accordance with implementations of the present disclosure.

FIG. 14 is an example fusion based regional body composition generation process, in accordance with implementations of the present disclosure.

DETAILED DESCRIPTION

As is set forth in greater detail below, implementations of the present disclosure are directed to the collection of two-dimensional ("2D") color body images of a body of a user and the determination of one or more regional body compositions values of the body based on the collected 2D image. Regional body composition values are values for different aspects of the body for different regions of the body. For example, body regions may include, but are not limited to, the full body, left arm, right arm, left leg, right leg, trunk, android, gynoid, etc. In other examples, regions of the body may be more specific or less specific. For example, more specific body regions may include upper left arm, lower left arm, left hand, upper torso, lower torso, etc. Less specific body regions may include left side, right side, upper body, lower body, etc. Body composition values for the different body regions may include, but are not limited to fat tissue mass, fat tissue percentage, lean tissue mass, lean tissue percentage, bone mineral density, bone mineral content, visceral fat, skeletal muscle mass, muscle mass percentage, etc. In some implementations, the 2D images may be processed to determine one or more body dimensions of the body. For example, body dimensions include, but are not limited to, shoulder circumference, chest circumference, waist circumference, hip circumference, inseam length, bicep circumference, leg circumference, waist to hip ratio, chest to waist ratio, waist to height ratio, etc. Also disclosed is the generation and presentation of a 3D body model from the 2D color body images.

Two-dimensional color body images may be obtained from any device that includes a 2D camera, such as cell phones, tablets, laptops, etc. In other implementations, the 2D color body images may be obtained from any other source, such as data storage. The 2D color body images may be sent by an application executing on the device to remote computing resources that process the 2D color body images to determine personalized 3D body features, to generate a personalized 3D body model of the body of the user, to determine body dimensions of the body represented in the 2D image, and/or to generate regional body composition values for different regions of the body represented in the 2D image.

The application executing on the portable device receives the current body dimension information, current regional body composition values, and personalized 3D body features, generates the personalized 3D body model, and presents some or all of the body dimensions, some or all of the regional body composition values, and/or the personalized 3D body model to the user. In some implementations, the user may interact with the personalized 3D body model to view different sides of the personalized 3D body model.

Figure 1:
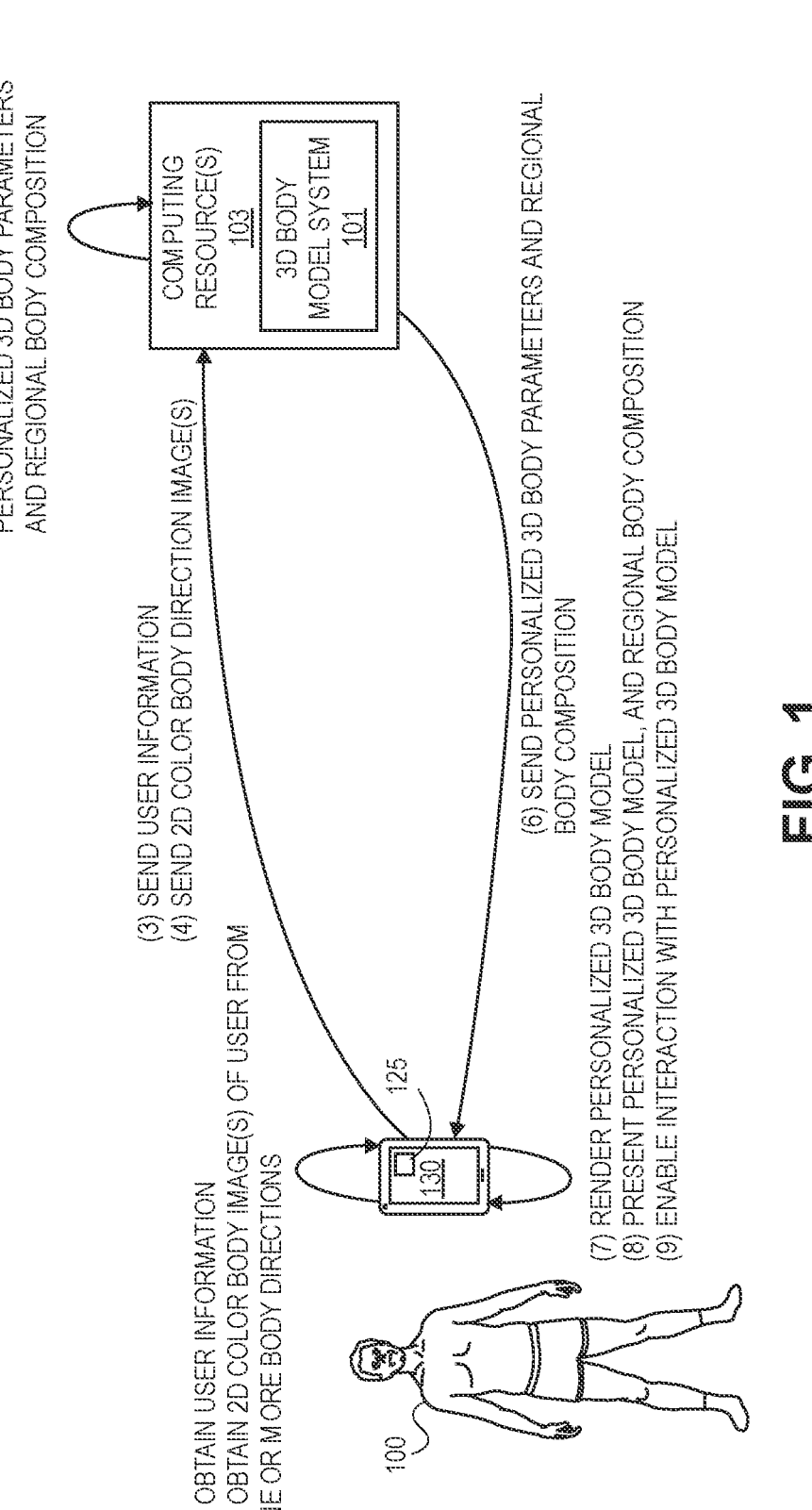
FIG. 1 is a transition diagram of two-dimensional color body image collection and processing to produce regional body composition values for different regions of the body and/or a personalized three-dimensional body model of that body that may be presented back to the user, in accordance with implementations of the present disclosure.
Figure 2:
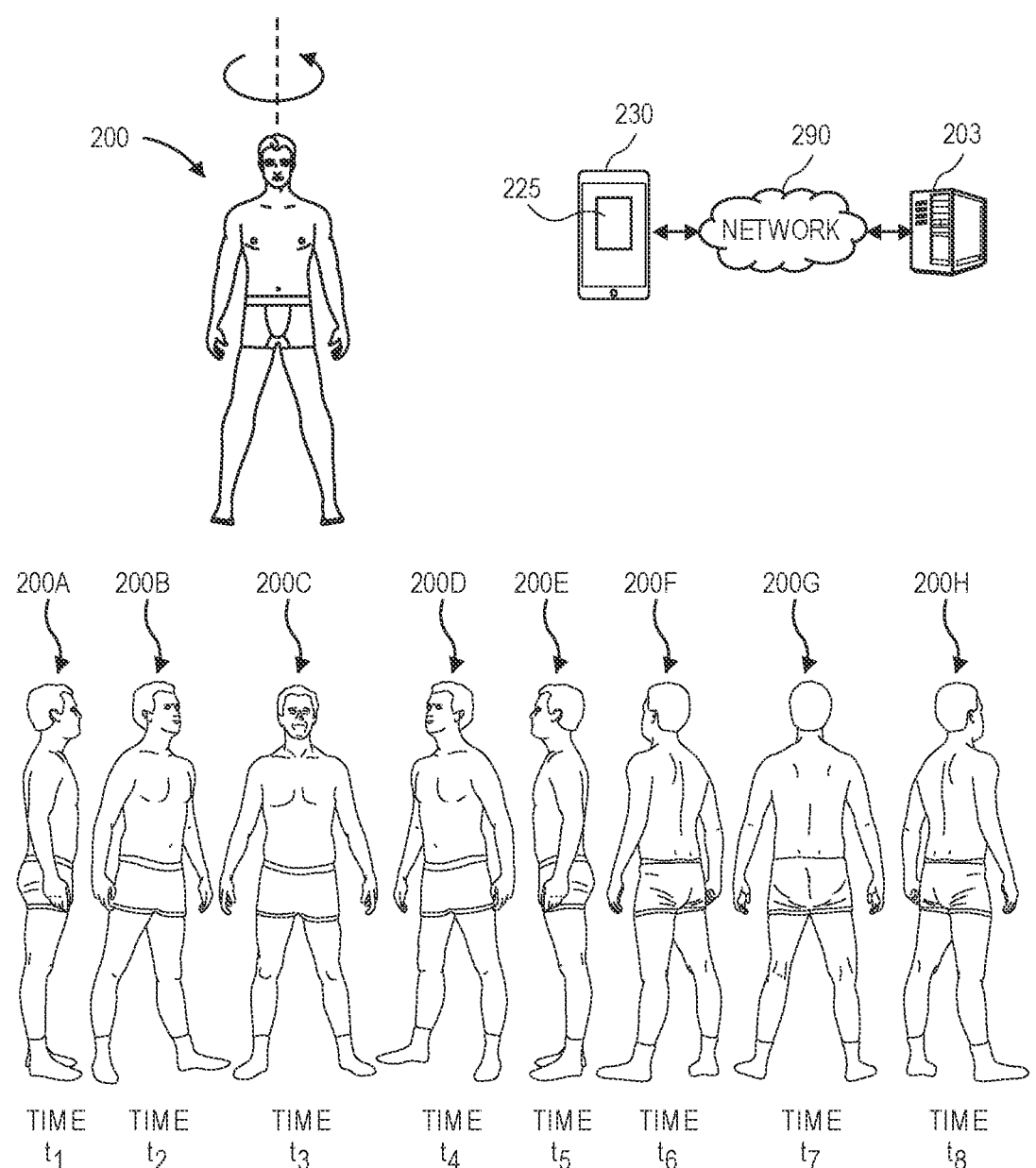
FIG. 2 illustrates different body directions of a body that may be captured in two-dimensional color body images and used to produce regional body composition values and/or a personalized three-dimensional body model, in accordance with implementations of the present disclosure.

FIG. 1 is a transition diagram of 2D color body image collection and processing to produce a personalized 3D body model of a body of a user 100, body dimensions of the body of the user, and/or regional body composition values that may be presented back to the user, in accordance with implementations of the present disclosure. FIG. 2 illustrates examples of different orientations or body directions of a body of a user 200, in accordance with implementations of the present disclosure.

In some implementations, a user 100/200 may execute an application 125/225 on a portable device 130/230, such as a cellular phone, tablet, laptop, etc., that includes an imaging element (e.g., camera) and interact with the application. The imaging element may be any conventional imaging element, such as a standard 2D Red, Green, Blue ("RGB") digital camera that is included on many current portable devices. Likewise, images, as discussed herein, may be still images generated by the imaging element and/or images or frames extracted from video generated by the imaging element. As used herein a body image, color body image, 2D color body images, or 2D images may be any form of 2D color body image, such as a color body image generated by an RGB digital camera of a portable device.

The user 100/200 may provide user information, such as username, password, etc., to the application 125/225 so that the application can identify the user and determine a user account associated with the user. Likewise, the user 100/200 may provide other user information, such as body information, including but not limited to weight, height, age, gender, ethnicity, etc., referred to herein as "known body traits." The user 100/200 may select or decide which known body traits or other user information is provided or choose not to provide any such information. In addition, in some implementations, the user 100/200 may interact with the application 125/225 executing on the portable device 130/230 without providing any user identifying information (e.g., operate as a guest to the application) and/or known body traits.

Upon user identification and/or receipt of user information, the user 100/200 positions the portable device 130/230 such that a field of view of the imaging element of the portable device is substantially horizontal and facing toward the user. In some implementations, the application 125/225 executing on the portable device 130/230 may provide visual and/or audible instructions that guide the user 100/200 in the placement and positioning of the portable device 130/230. For example, the application 125/225 may instruct the user 100/200 to place the portable device 130/230 between waist and head height of the user and in a substantially vertical direction (e.g., between 2 and 10 degrees of vertical) such that the imaging element is pointed toward the user and the field of view of the imaging element is substantially horizontal.

In some implementations, the application 125/225 may request that the user 100/200 wear a minimal amount of clothing, such as undergarments shown in FIGS. 1 and 2. By wearing minimal clothing, processing of the 2D color body image may be more accurate.

Once the portable device is properly positioned, 2D color body images of the user 100/200 are captured by the imaging element of the portable device 130/230. The 2D color body images are processed to determine that the user 100/200 is in a defined pose, such as an "A Pose," and to determine a body direction of the body of the user with respect to the imaging element. The defined pose may be any body position that enables image capture of components of the body. In one example, the defined pose is an "A Pose" in which the arms are separated from the sides of the body and the legs are separated, for example by separating the feet of the body to about shoulder width. The "A Pose" allows image processing of 2D color body images to distinguish between body regions (e.g., legs, arms, torso) from different angles and also aids in body direction determination. The body direction may be any direction or orientation of the body with respect to the imaging element. Example body directions include, but are not limited to, a front side body direction in which the body is facing the imaging element, a right side body direction in which the body is turned such that a right side of the body is facing the imaging element, a left side body direction in which a left side of the body is facing the imaging element, and a back side body direction in which a back of the body is facing the imaging element. As will be appreciated, any number of body directions and corresponding orientations of the body may be utilized with the disclosed implementations and the four discussed (front side, right side, back side, and left side) are provided only as examples.

In some implementations, the application 125/225 executing on the portable device 130/230 may guide the user 100/200 through different body directions and select one or more 2D images as representative of each body direction. For example, referring to FIG. 2, an application 225 executing on the portable device 230 may guide the user 200 into the proper pose, such as the "A Pose" illustrated by the body 200 of the user and then guide the user through a series of body directions 200A, 200B, 200C, 200D, 200E, 200F, 200G, and 200H in which the user rotates their body to the requested body direction and remains in the "A Pose" while 2D color body images are generated and one or more of those 2D color body images are selected by the application as a 2D body direction image corresponding to the current body direction of the body of the user. In the example illustrated in FIG. 2, eight different 2D body direction images are selected by the application 225 executing on the portable device 230, one for each respective body direction 200A, 200B, 200C, 200D, 200E, 200F, 200G, and 200H. In other implementations, additional or fewer body direction images may be obtained and utilized.

Returning back to FIG. 1, as each 2D body direction image is selected by the application, or after all 2D body direction images are selected, the 2D body direction images are sent from the application 125/225 executing on the portable device 130/230 via a network 290 (FIG. 2) to remote computing resources 103/203 for further processing. In addition, the user information, such as known body traits, provided to the application 125/225 by the user 100/200 may be sent from the application executing on the portable device 130/230 to the remote computing resources 103/203. In other implementations, all processing may be done on the portable device 130/230. In still other examples, as images are generated, the images may be sent to the remote computing resources 103/203 and processed by the remote computing resources 103/203 to select the body direction images.

The remote computing resources 103/203 may include a 3D body model system 101 that receives the user information and/or the 2D body direction images and processes those images using one or more neural networks, such as a convolutional neural network ("CNN"), to generate personalized 3D body features corresponding to a personalized 3D body model of the body of the user 100/200. In addition, one or more of the 2D body direction images, such as front side 2D body direction image may be processed to determine one or more regional body composition values for one or more regions of the body, such as fat tissue values, lean tissue values, bone mineral density values, skeletal muscle mass values, etc. Still further, one or more of the 2D body direction images may be processed, as discussed further below, to determine one or more body dimensions of the user, such as shoulder circumference, waist circumference, waist-to-hip ratio, etc.

The 3D body model system 101, upon generating the personalized 3D body features, body dimensions and/or regional body composition values, sends the personalized 3D body features, body dimensions, and regional body composition values back to the application 125/225 executing the portable device 130/230. The application 125/225, upon receipt of the personalized 3D body features, body dimensions, and regional body composition values generates, from the personalized 3D body features, a personalized 3D body model 101 that is representative of the body of the user 100/200 and presents the personalized 3D body model, one or more body dimensions, and/or one or more regional body composition values on a display of the portable device 130/230.

In addition to rendering and presenting the personalized 3D body model, one or more body dimensions, and/or one or more regional body composition values may be presented. In some implementations, the user 100/200 can interact with the presented personalized 3D body model, body dimensions, and regional body composition values. For example, the user 100/200 may view historical information that was previously collected for the user via the application 125/225. The user 100/200 may also interact with the presented personalized 3D body model to rotate and/or turn the presented personalized 3D body model. For example, if the portable device 130/230 includes a touch-based display, the user 100/200 may use the touch-based display to interact with the application 125/225 and rotate the presented personalized 3D body model to view different views (e.g., front, side, back) of the personalized 3D body model.

Likewise, in some implementations, the user 100/200 may view body dimensions and/or regional body composition values with respect to a larger population or cohort to which the user is associated (e.g., based on age, fitness level, height, weight, gender, etc.). For example, the user 100/200 may view aggregated and anonymized body dimension information and/or regional body composition values based on other people that are within five years of age of the user and of a same gender as the user.

Figure 3A:
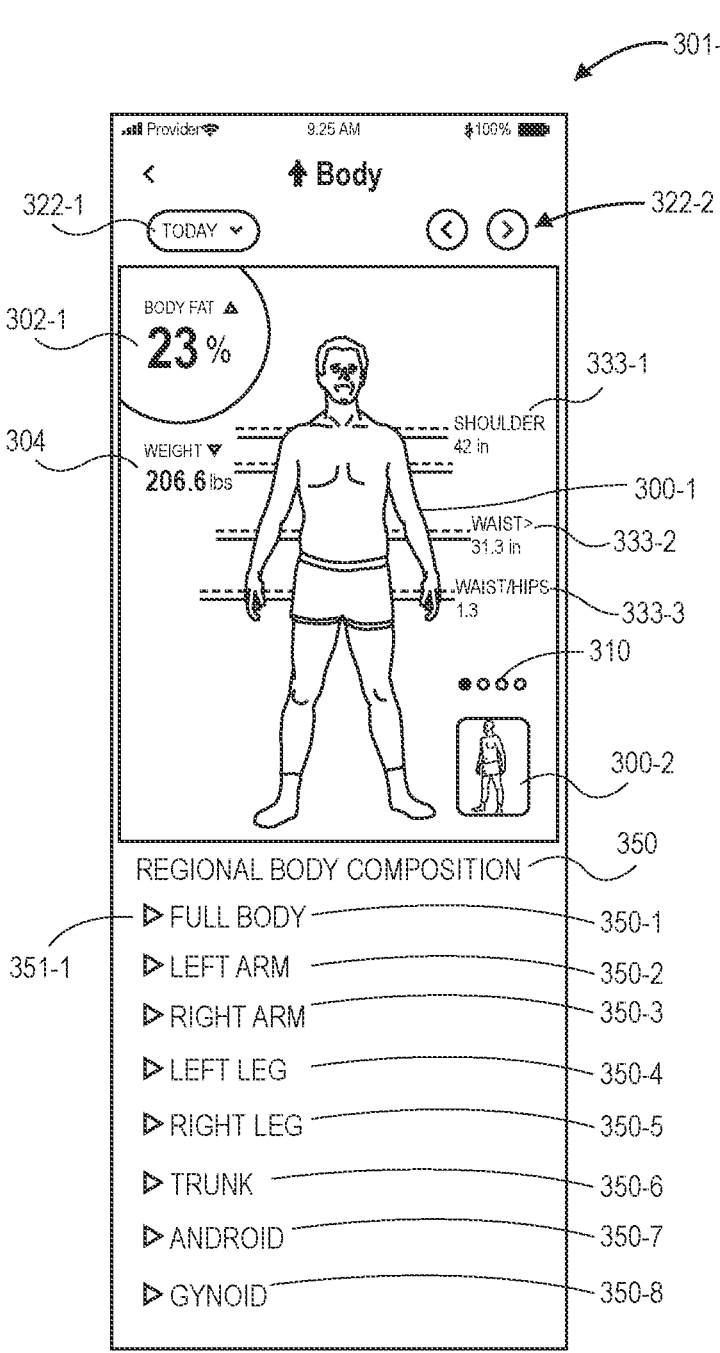
FIG. 3A is a user interface illustrating a captured two-dimensional color body image, corresponding body dimensions, and different body regions for which regional body composition values have been determined from at least the two-dimensional color body image, in accordance with implementations of the present disclosure.

FIG. 3A is a user interface 301-1 presented by an application executing on a portable device, such as the application 125/225 executing on the portable device 130/230 discussed above with respect to FIGS. 1 and 2, in accordance with implementations of the present disclosure.

In this example, the user interface 301-1 illustrates a 2D body direction image 300-1 captured by an imaging element of the portable device that was used to generate and present a personalized 3D body model, corresponding body dimension information, and corresponding regional body composition values for different regions of the body. In this example, the illustrated user interface 301-1 shows the 2D body direction image, body dimensions, including the shoulder circumference 333-1, waist circumference 333-2, and waist/hip ratio 333-3, and regional body composition values for the total body, including the total body fat percentage 302-1 determined for the body, and the weight 304 of the body. As will be appreciated, additional or less body dimensions and/or regional body composition values may be included on the user interface 301-1. For example, additional body dimensions, such as bicep circumference, waist to height ratio, thigh circumference, etc., may optionally be presented on the user interface. In some examples, a user may select which body dimensions and/or regional body composition values are presented. Additionally, other regions of the body for which body composition values are available are indicated in the user interface in the Regional Body Composition 350 portion of the user interface 301-1. Other body regions for which regional body composition values have been computed and are available for viewing through the user interface 301-1 may include, but are not limited to, Full Body 350-1, Left Arm 350-2, Right Arm 350-3, Left Leg 350-4, Right Leg 350-5, Trunk 350-6, Android 350-7, and Gynoid 350-8. In other implementations, additional, fewer, and/or different body regions may be presented.

As discussed further below; the body dimensions may be determined from the 2D body direction image 300-1. Likewise, as discussed further below, regional body composition values for different regions of the body may be determined from the 2D body direction image 300-1.

A user interacting with the user interface 301-1 may also select to view other 2D body direction images that were used to generate a personalized 3D body model, other body dimensions determined for the body, and/or other regional body composition values determined for the body by selecting the indicators 310, swiping or otherwise interacting with the user interface 301-1 to alter the currently presented 2D body direction image 300-1, and/or by selecting the control arrows, such as control arrow 351-1 next to the indications of the body regions 350-1 through 350-8 for which regional body composition values are available. The user may also alternate between a view of 2D body direction images 300-1, as illustrated in the user interface 301-1 of FIG. 3A and the rendered and presented personalized 3D body model 300-2, as illustrated in the small image presentation of the personalized 3D body model 300-2 in FIG. 3A and as illustrated as the primary image 300-2 in user interface 301-2 of FIG. 3B.

Figure 3B:
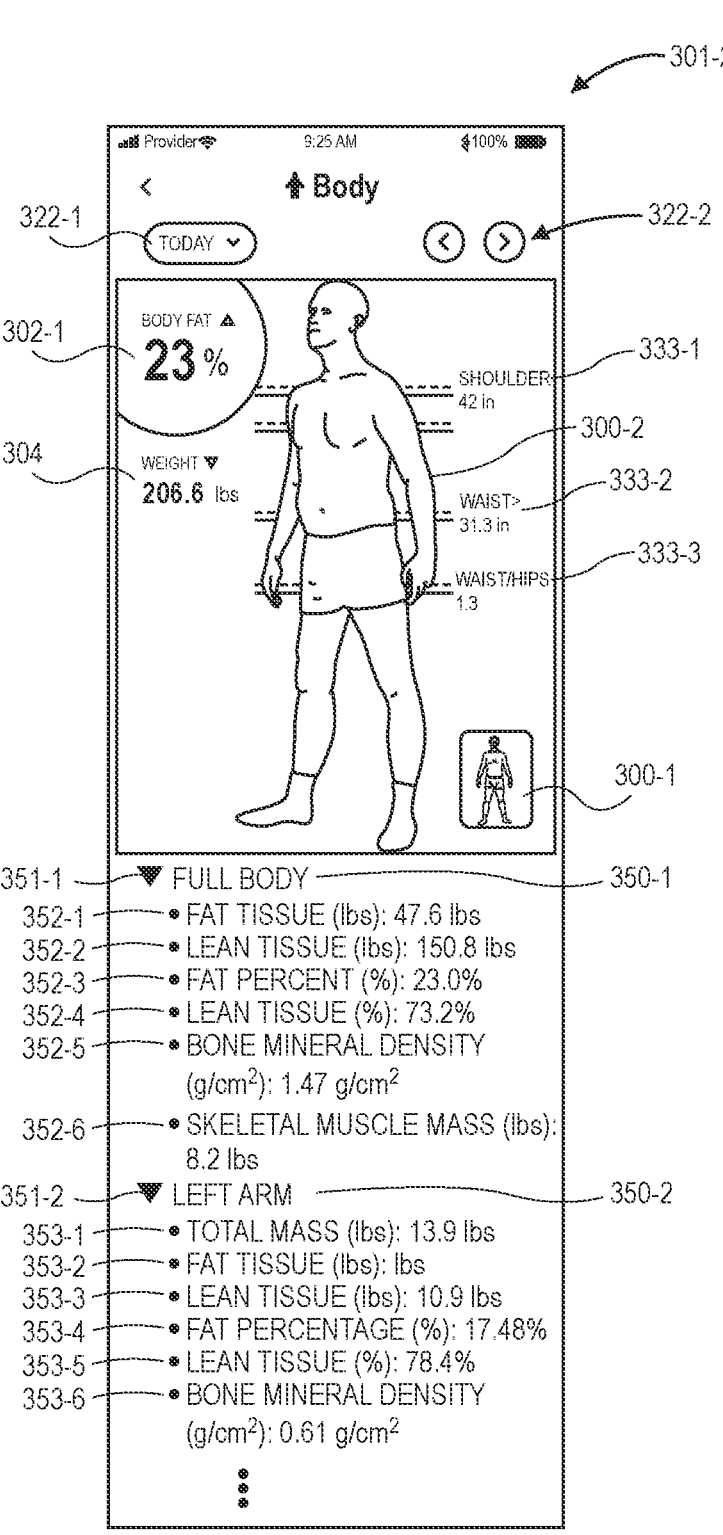
FIG. 3B is a user interface illustrating a personalized three-dimensional body model, and regional body composition values determined for the full body and the left arm of the body, generated from a two-dimensional color body image, in accordance with implementations of the present disclosure.

Referring to FIG. 3B, the user may interact with, to rotate and/or change the view of the personalized 3D body model 300-2 by directly interacting with the personalized 3D body model 300-2. For example, the user may rotate the presentation of the personalized 3D body model 300-2 to view different portions of the personalized 3D body model, zoom out to view more of the personalized 3D body model, or zoom in to view details corresponding to a portion of the personalized 3D body model. In addition, the user may select one or more of the control arrows, such as control arrows 351-1 or 351-2 to view regional body composition values determined for those regions of the body. In the illustrated example, the user has selected the control arrow 351-1 corresponding to the full body 350-1 region and is presented with the corresponding regional body composition values of fat tissue mass 352-1, lean tissue mass 352-2, fat percentage 352-3, lean tissue percentage 352-4, bone mineral density 352-5, and skeletal muscle mass 352-6. In addition, the user has selected the control arrow 351-2 corresponding to the left arm 350-2 of the body of the user and is presented with the corresponding regional body composition values of total mass 353-1, fat tissue mass 353-2, lean tissue mass 353-3, fat percentage 353-4, lean tissue percentage 353-5, and bone mineral density 353-6.

In some implementations, if the user has utilized the application 125/225 over a period of time to generate multiple instances of personalized 3D body models of the user 100/200, the user interface may also present historical regional body composition values and/or body dimensions corresponding to the different dates in which 2D color body images of the body of the user were captured and used to generate a personalized 3D body model, body dimensions, and regional body composition values of the body of the user. In addition to viewing historical body dimensions and/or regional body composition values, the user 100/200 may also access and view either the 2D color body images that were collected at those prior points in time and/or view the personalized 3D body models generated from those prior 2D color body images, through selection of the date control 322-1 or the arrow control 322-2.

Figure 4:
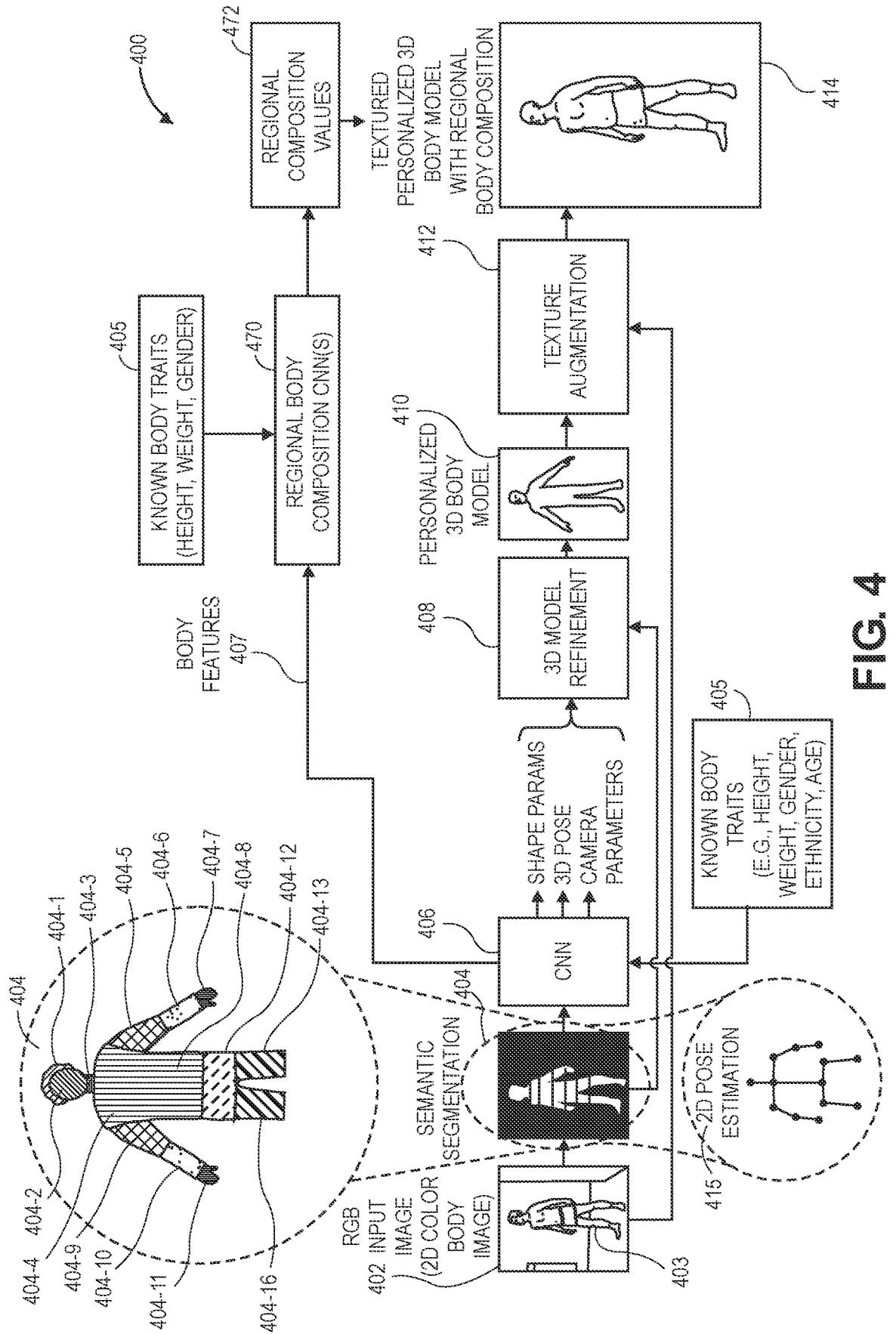
FIG. 4 is a transition diagram of processing two-dimensional color body images to produce a personalized three-dimensional model of that body and corresponding regional body composition values, in accordance with implementations of the present disclosure.

FIG. 4 is a transition diagram 400 of processing 2D color body images of a body to produce a personalized 3D body model and regional body composition values for regions of that body, in accordance with implementations of the present disclosure.

3D modeling and regional body composition value determination of a body from 2D color body images begins with the receipt or creation of a 2D color body image 402 that includes a representation of the body 403 of the user to be modeled. As discussed above, 2D color body images 402 for use with the disclosed implementations may be generated using any conventional imaging element, such as a standard 2D Red, Green, Blue ("RGB") digital camera that is included on many current portable devices (e.g., tablets, cellular phones, laptops, etc.). The 2D color body image 402 may be a still image generated by the imaging element or an image extracted from video generated by the imaging element. Likewise, any number of images 402 may be used with the disclosed implementations.

As discussed, the user may be instructed to stand in a particular orientation (e.g., front facing toward the imaging element, side facing toward the imaging element, back facing toward the imaging element, etc.) and/or to stand in a particular pose, such as an "A pose." Likewise, the user may be instructed to stand a distance from the camera such that the body of the user is completely or partially included in a field of view of the imaging element and represented in the generated image 402. Still further, in some implementations, the imaging element may be aligned or positioned at a fixed or stationary point and at a fixed or stationary angle so that images generated by the imaging element are each from the same perspective and encompass the same field of view.

As will be appreciated, a user may elect or opt-in to having a personalized 3D body model of the body of the user generated and may also select whether the generated personalized 3D body model and/or other information, such as determined regional body composition values, may be used for further training of the disclosed implementations and/or for other purposes.

The 2D color body image 402 that includes a representation of the body 403 of the user may then be processed to produce a segmented silhouette 404 of the body 403 of the user represented in the image 402 and for generating a 2D pose estimation 415 of the pose of the body 403 represented in the 2D image. A variety of techniques may be used to generate the segmented silhouette 404 and/or the 2D pose estimation 415. For example, background subtraction may be used to subtract or black out pixels of the image that correspond to a background of the image while pixels corresponding to the body 403 of the user (i.e., foreground) may be assigned a white or other color values. In another example, a semantic segmentation algorithm may be utilized to label background and body (foreground) pixels and/or to identify different segments of the body. For example, a convolutional neural network ("CNN") may be trained with a semantic segmentation algorithm to determine bodies, such as human bodies, in images and/or to determine body segments (e.g., head segment, neck segment, torso segment, left arm segment, etc.).

In addition, or as an alternative thereto, the segmented silhouette 404 may be segmented into one or more body segments, such as hair segment 404-1, head segment 404-2, neck segment 404-3, upper clothing segment 404-4, upper left arm 404-5, lower left arm 404-6, left hand 404-7, torso 404-8, upper right arm 404-9, lower right arm 404-10, right hand 404-11, lower clothing 404-12, upper left leg 404-13, upper right leg 404-16, etc. For example, the CNN may be trained with a semantic segmentation algorithm to predict for each pixel of an image, the likelihood that the pixel corresponds to a segment label (e.g., hair, upper clothing, lower clothing, head, upper right arm, etc.). For example, the CNN may be trained to process each 2D color body image and output, for each pixel of each image, a vector that indicates a probability for each label that the pixel corresponds to that label. For example, if there are twenty-three labels (e.g., body segments) for which the CNN is trained, the CNN may generate, for each pixel of a 2D image, a vector that includes a probability score for each of the twenty-three labels indicating the likelihood that the pixel corresponds to the respective label. As a result, each pixel of an image may be associated with a segment based on the probability scores indicated in the vector. For segments for which the CNN is trained but are not represented in the 2D image, the CNN will provide low or zero probability scores for each label indicated in the vector, thereby indicating that the segment is not visible in the 2D color body image.

In some implementations, the silhouette 404 of the body of the user 403 may be normalized in height and centered in the image 402 to produce one or more normalized color body image(s). This may be done to further simplify and standardize inputs to a CNN to those on which the CNN was trained. Likewise, a silhouette 404 of the body of the user 403 may be preferred over the representation of the body of the user so that the CNN can focus only on body shape and not skin tone, texture, clothing, etc.

2D pose estimation 415 may be determined, for example based on object detection, processing the image to determine body joint locations, etc. For example, a CNN may be trained to determine, for each pixel of the body 403 represented in the image a likelihood that the pixel corresponds to a joint (e.g., ankle, knee, wrist, etc.). Based on the determined probability scores, joint locations may be determined. Based on the positioning of the determined joint locations, a 2D pose estimation may be determined for the pose of the body 403 represented in the 2D image, such as an A pose discussed above.

The silhouette 404 of the body may then be processed by one or more other CNNs 406 that are trained to determine body features representative of the body and to produce personalized 3D body features and/or 3D pose that are used to determine body dimensions of the body and a personalized 3D body model of the body. The body features 407 may be represented as a set of neural network weights representative of different aspects of the body. In some implementations, the CNN 406 may be trained for multi-mode input to receive as inputs to the CNN the silhouette 404, the 2D pose estimation 415, and/or one or more known body traits 405 of the body of the user. For example, a user may provide a height of the body of the user, a weight of the body of the user, a gender of the body of the user, the ethnicity of the body of the user, the age of the body of the user, etc., and the CNN 406 may receive one or more of those provided known body traits 405 as an input.

Based on the received inputs, the CNN 406 generates body features corresponding to the body 403 and personalized 3D body features, such as 3D joint locations, body volume, shape of the body, pose angles, etc. In some implementations, the CNN 406 may be trained to predict hundreds of shape parameters of the body 403 represented in the image 402.

Likewise, a personalized 3D body model 410 of the body 403 is generated based on the personalized 3D body features. For example, to generate the personalized 3D body model 410, the personalized 3D body features may be provided to a body model, such as the Shape Completion and Animation of People ("SCAPE") body model, a Skinned Multi-Person Linear ("SMPL") body model, etc., and the body model may generate the personalized 3D body model 410 of the body of the user 403 based on those predicted body features 407.

In some implementations, as discussed further below, personalized 3D model refinement 408 may be performed to refine or revise the generated personalized 3D body model 410 to better represent the body of the user 403. For example, the personalized 3D body model 410 may be compared to the representation of the body of the user 403 in the image 402 to determine differences between the shape of the body of the user 403 represented in the image 402 and the shape of the personalized 3D body model 410. Based on the determined differences, the silhouette 404 may be refined and the refined silhouette processed by the CNN 406 to produce a refined personalized 3D body model 410 of the body of the user 403. This refinement may continue until there is no or little difference between the shape of the body of the user 403 represented in the image 402 and the shape of the personalized 3D body model 410. In other implementations, a 2D model image 402 may be generated from the personalized 3D body model 410 and that 2D model image may be compared to the silhouette 404 and/or the 2D color body image to determine differences between the 2D model image and the 2D color body image or silhouette. Based on the determined differences, the personalized 3D body features and/or the personalized 3D body model 410 may be refined until the personalized 3D body model corresponds to the body of the user 403 represented in the 2D color body image 402 and/or the silhouette 404.

Still further, in some implementations, the personalized 3D body model 410 of the body of the user 403 may be augmented with one or more textures, texture augmentation 412, determined from the image 402 of the body of the user. For example, the personalized 3D body model 410 may be augmented to have a same or similar color to a skin color of the body of the user 403 represented in the image 402, clothing or clothing colors represented in the image 402 may be used to augment the personalized 3D body model, facial features, hair, hair color, etc., of the body of the user 403 represented in the image 402 may be determined and used to augment the personalized 3D body model, etc.

In addition to generation of a personalized 3D body model 410, the body features 407 determined for the body may also be processed by one or more regional body composition CNN(s) 470 that determine regional body composition values 472 for different regions of the body, as discussed further below. In some implementations, the regional body composition CNN(s) 470 may receive and process the determined body features 407. In other implementations, the regional body composition CNN(s) 470 may receive and process one or more of the silhouette(s) 404, the 2D color body image(s) 402, the background subtracted and normalized 2D color body image(s), etc.

The result of the processing illustrated in the transition 400 is a personalized 3D body model 414 or avatar representative of the body of the user, that has been generated from 2D color body images of the body of the user. In addition, determined regional body composition values 172 for different regions of the body may be determined and presented with the personalized 3D body model 414, as illustrated above.

Figure 5A:
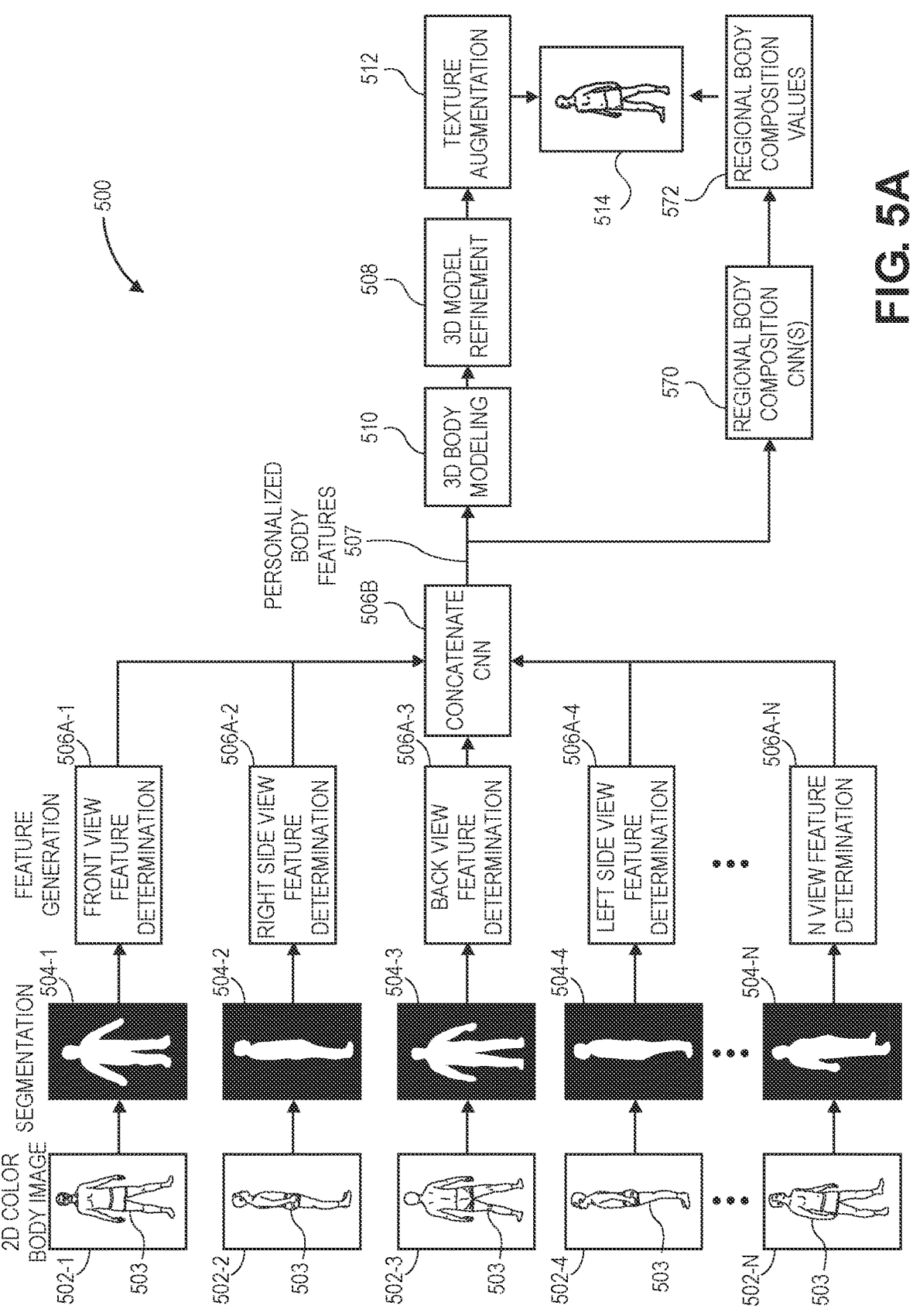
FIG. 5A is another transition diagram of processing two-dimensional color body images to produce a personalized three-dimensional model of that body and corresponding regional body composition values, in accordance with implementations of the present disclosure.

FIG. 5A is another transition diagram 500 of processing 2D color body images 502 of a body to produce a personalized 3D body model and regional body composition values of that body, in accordance with implementations of the present disclosure.

In some implementations, multiple 2D color body images of a body from different views (e.g., front view, side view; back view; three-quarter view, etc.), such as 2D color body images 502-1, 502-2, 502-3, 502-4 through 502-N may be utilized with the disclosed implementations to generate a personalized 3D body model of the body. In the illustrated example, the first 2D color body image 502-1 is an image of a human body 503 oriented in a front view facing a 2D imaging element. The second 2D color body image 502-2 is an image of the human body 503 oriented in a first side view facing the 2D imaging element. The third 2D color body image 502-3 is an image of the human body 503 oriented in a back view facing the 2D imaging element. The fourth 2D color body image 502-4 is an image of the human body 503 oriented in a second side view facing the 2D imaging element. As will be appreciated, any number of 2D color body images 502-1 through 502-N may be generated with the view of the human body 503 in any number or orientations with respect to the 2D imaging element.

Each of the 2D color body images 502-1 through 502-N are processed to segment pixels of the image that represent the human body from pixels of the image that do not represent the human body to produce a silhouette 504 of the human body as represented in that image. Segmentation may be done through, for example, background subtraction, semantic segmentation, etc. In one example, a baseline image of the background may be known and used to subtract out pixels of the image that correspond to pixels of the baseline image, thereby leaving only foreground pixels that represent the human body. The background pixels may be assigned RGB color values for black (i.e., 0,0,0). The remaining pixels may be assigned RGB values for white (i.e., 255, 255, 255) to produce the silhouette 504 or binary segmentation of the human body.

In another example, a CNN utilizing a semantic segmentation algorithm may be trained using images of human bodies or simulated human bodies to train the CNN to distinguish between pixels that represent human bodies and pixels that do not represent human bodies and optionally to identify pixels of different segments of the human body. In such an example, the CNN may process the image 502 and indicate or label pixels that represent the body (foreground) and pixels that do not represent the body (background). The background pixels may be assigned RGB color values for black (i.e., 0,0,0). The remaining pixels may be assigned RGB values for white (i.e., 255, 255, 255) to produce the silhouette or binary segmentation of the human body. For segmentation, pixels may be further processed to determine body segments of the body to which the pixels correspond.

In other implementations, other forms or algorithms, such as edge detection, shape detection, etc., may be used to determine pixels of the image 502 that represent the body 403 and pixels of the image 502 that do not represent the body and a silhouette 504 of the body produced therefrom.

Returning to FIG. 5A, the first 2D color body image 502-1 is processed to segment a plurality of pixels of the first 2D color body image 502-1 that represent the human body 503 from a plurality of pixels of the first 2D color body image 502-1 that do not represent the human body, to produce a front silhouette 504-1 of the human body. The second 2D color body image 502-2 is processed to segment a plurality of pixels of the second 2D color body image 502-2 that represent the human body 503 from a plurality of pixels of the second 2D color body image 502-2 that do not represent the human body, to produce a first side silhouette 504-2 of the human body. The third 2D color body image 502-3 is processed to segment a plurality of pixels of the third 2D color body image 502-3 that represent the human body 503 from a plurality of pixels of the third 2D color body image 502-3 that do not represent the human body, to produce a back silhouette 504-3 of the human body. The fourth 2D color body image 502-4 is processed to segment a plurality of pixels of the fourth 2D color body image 502-4 that represent the human body 503 from a plurality of pixels of the fourth 2D color body image 502-4 that do not represent the human body, to produce a second side silhouette 504-4 of the human body. Processing of the 2D color body images 502-1 through 502-N to produce silhouettes 504-1 through 504-N from different orientations of the human body 503 may be performed for any number of images 502.

As discussed above with respect to FIG. 4, in some implementations, the silhouette 504 may be segmented into different body segments by processing the pixels of the 2D image to determine a likelihood that the pixel corresponds to a segment label (e.g., hair, upper clothing, lower clothing, head, upper right arm, upper left leg, etc.).

In some implementations, in addition to generating a silhouette 504 from the 2D color body image 502, the silhouette may be normalized in size and centered in the image. For example, the silhouette may be cropped by computing a bounding rectangle around the silhouette 504. The silhouette 504 may then be resized according to s, which is a function of a known height h of the user represented in the 2D color body image (e.g., the height may be provided by the user):

$$s = h * \frac{0.8 * image_h}{\mu_h} \tag{1}$$

Where $image_h$ is the input image height, which may be based on the pixels of the image, and $\mu_h$ is the average height of a person (e.g., ~160 centimeters for females: ~176 centimeters for males).

Each silhouette 504 representative of the body 503 may then be processed to determine body traits or features of the human body. For example, different CNNs may be trained using silhouettes of bodies, such as human bodies, from different orientations with known features. In some implementations, different CNNs may be trained for different orientations. For example, a first CNN 506A-1 may be trained to determine front view features from front view silhouettes 504-1. A second CNN 506A-2 may be trained to determine right side features from right side silhouettes 504-2. A third CNN 506A-3 may be trained to determine back view features from back view silhouettes 504-3. A fourth CNN 506A-4 may be trained to determine left side features from left side silhouettes 504-4. Different CNNs 506A-1 through 506A-N may be trained for each of the different orientations of silhouettes 504-1 through 504-N. Alternatively, one CNN may be trained to determine features from any orientation silhouette.

In implementations that utilize multiple images of the body 503 to produce multiple sets of features, such as the example illustrated in FIG. 5A, those features may be concatenated, and the concatenated features processed together with a CNN to generate a set of personalized body features 507. For example, a CNN may be trained to receive features generated from different silhouettes 504 to produce personalized body features 507. The personalized body features 507 may indicate any aspect or information related to the body 503 represented in the images 502. For example, the personalized body features 507 may indicate 3D joint locations, body volume, shape of the body, pose angles, neural network weights corresponding to the body, etc. In some implementations, the concatenated CNN 506B may be trained to predict hundreds of personalized body features 507 corresponding to the body 503 represented in the images 502.

Utilizing the personalized body features 507 and/or one or more of the segmented color body images or features determined therefrom, a regional body composition CNN 570 processes the features and determines regional body composition values 572 for the body, as discussed further below. As noted above, in some implementations, the regional body composition CNN(s) 470 may receive and process one or more of the determined body features 407, silhouette(s) 404, the 2D color body image(s) 402, the background subtracted and normalized 2D color body image(s), etc. Likewise, a personalized 3D body model of the body is generated based on the personalized body features 507. For example, the personalized body features 507 may be provided to a body model, such as the SCAPE body model, the SMPL body model, etc., and the body model may generate the personalized 3D body model of the body 503 represented in the images 502 based on those personalized body features 507.

In the illustrated example, personalized 3D model refinement 508 may be performed to refine or revise the generated personalized 3D body model to better represent the body 503 represented in the 2D color body images 502. For example, the personalized 3D body model may be compared to the body 503 represented in one or more of the 2D color body images 502 to determine differences between the shape of the body 503 represented in the 2D color body image 502 and the shape of the personalized 3D body model generated from the body features. In some implementations, the personalized 3D body model may be compared to a single image, such as image 502-1. In other implementations, the personalized 3D body model may be compared to each of the 2D color body images 502-1 through 502-N in parallel or sequentially. In still other implementations, one or more 2D model images may be generated from the personalized 3D body model and those 2D model images may be compared to the silhouettes 504 and/or the 2D color body images 502 to determine differences between the 2D model images and the silhouette/2D color body images.

Comparing the personalized 3D body model and/or a 2D model image with a 2D color body image 502 or silhouette 504 may include determining an approximate pose of the body 503 represented in the 2D color body image and adjusting the personalized 3D body model to the approximate pose. The personalized 3D body model or rendered 2D model image may then be overlaid or otherwise compared to the body 503 represented in the 2D color body image 502 and/or represented in the silhouette 504 to determine a difference between the personalized 3D body model and the 2D color body image.

Based on the determined differences between the personalized 3D body model and the body 503 represented in the 2D color body image 502, the silhouette 504 generated from that image may be refined to account for those differences. For example, if the personalized 3D body model is compared with the body 503 represented in the first image 502-1 and differences are determined, the silhouette 504-1 may be refined based on those differences. Alternatively, the body features and/or the personalized 3D body model may be refined to account for those differences.

If a silhouette 504 is refined as part of the personalized 3D model refinement 508, the refined silhouette may be processed to determine refined features for the body 503 represented in the 2D color body image 502 based on the refined silhouette. The refined features may then be concatenated with the features generated from the other silhouettes or with refined features generated from other refined silhouettes that were produced by the personalized 3D model refinement 508. For example, the personalized 3D model refinement 508 may compare the generated personalized 3D body model with the body 503 as represented in two or more 2D color body images 502, such as a front image 502-1 and a back image 502-3, differences determined for each of those images, refined silhouettes generated from those differences and refined front view features and refined back view features generated. Those refined features may then be concatenated with the two side view features to produce refined body model features. In other implementations, personalized 3D body model refinement 508 may compare the personalized 3D body model with all views of the body 503 represented in the 2D color body images 502 to determine differences and generate refined silhouettes for each of those 2D color body images 502-1 through 502-N. Those refined silhouettes may then be processed by the CNNs 506A-1 through 506A-N to produce refined features and those refined features concatenated to produce refined body features 507. Finally, the refined body features 507 may be processed by personalized 3D modeling 510 to generate a refined personalized 3D body model. This process of personalized 3D refinement may continue until there is no or limited difference (e.g., below a threshold difference) between the generated personalized 3D body model and the body 503 represented in the 2D color body images 502.

In another implementation, personalized 3D model refinement 508 may sequentially compare the personalized 3D body model with representations of the body 503 in the different 2D color body images 502. For example, personalized 3D model refinement 508 may compare the personalized 3D body model with a first representation of the body 503 in a first 2D color body image 502-1 to determine differences that are then used to generate a refined silhouette 504-1 corresponding to that first 2D color body image 502-1. The refined silhouette 504-1 may then be processed to produce refined features and those refined features may be concatenated 506B with the features generated from the other silhouettes 504-2 through 504-N to generate refined body features, which may be used to generate a refined personalized 3D body model. The refined personalized 3D body model may then be compared with a next image of the plurality of 2D color body images 502 to determine any differences and the process repeated. This process of personalized 3D refinement may continue until there is no or limited difference (e.g., below a threshold difference) between the generated personalized 3D body model and the body 503 represented in the 2D color body images 502.

In some implementations, the generated personalized 3D refinement generated by the 3D model refinement 508, may be provided to the regional body composition CNN(s) 570 as an input that is used to determine regional body compositions for the CNN.

In some implementations, upon completion of personalized 3D model refinement 508, the personalized 3D body model of the body 503 represented in the 2D color body images 502 may be augmented with one or more textures, texture augmentation 512, determined from one or more of the 2D color body images 502-1 through 502-N. For example, the personalized 3D body model may be augmented to have a same or similar color to a skin color of the body 503 represented the 2D color body images 502, clothing or clothing colors represented in the 2D color body images 502 may be used to augment the personalized 3D body model, facial features, hair, hair color, etc., of the body 503 represented in the 2D color body image 502 may be determined and used to augment the personalized 3D body model.

Similar to personalized 3D model refinement, the approximate pose of the body in one of the 2D color body images 502 may be determined and the personalized 3D body model adjusted accordingly so that the texture obtained from that 2D color body image 502 may be aligned and used to augment that portion of the personalized 3D body model. In some implementations, alignment of the personalized 3D body model with the approximate pose of the body 503 may be performed for each 2D color body image 502-1 through 502-N so that texture information or data from the different views of the body 503 represented in the different 2D color body images 502 may be used to augment the different poses of the resulting personalized 3D body model.

The result of the processing illustrated in the transition 500 is a personalized 3D body model 514 or avatar representative of the body of the user, that has been generated from 2D color body images 502 of the body 503 of the user. In addition, determined body dimensions may be presented with the personalized 3D body model, as illustrated above.

Figure 5B:
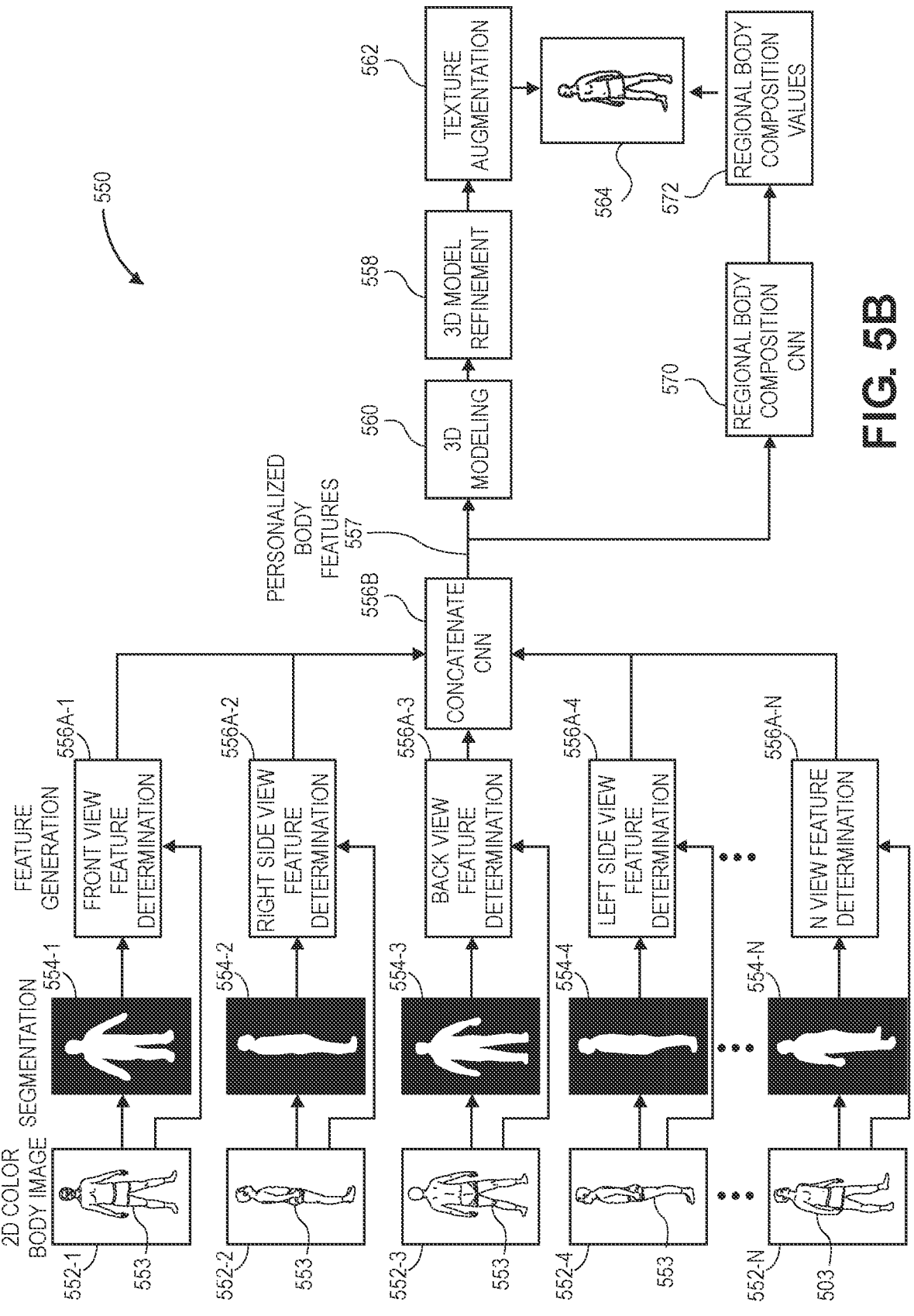
FIG. 5B is another transition diagram of processing two-dimensional color body images to produce a personalized three-dimensional model of that body and corresponding regional body composition values, in accordance with implementations of the present disclosure.

FIG. 5B is another transition diagram 550 of processing 2D color body images 552 of a body 553 to produce a personalized three-dimensional model of that body and corresponding regional body composition values for regions of that body, in accordance with implementations of the present disclosure.

In some implementations, multiple 2D color body images of a body from different views (e.g., front view, side view, back view; three-quarter view, etc.), such as 2D color body images 552-1, 552-2, 552-3, 552-4 through 552-N may be utilized with the disclosed implementations to generate a personalized 3D body model of the body. In the illustrated example, the first 2D color body image 552-1 is an image of a human body 553 oriented in a front view facing a 2D imaging element. The second 2D color body image 552-2 is an image of the human body 553 oriented in a first side view facing the 2D imaging element. The third 2D color body image 552-3 is an image of the human body 553 oriented in a back view facing the 2D imaging element. The fourth 2D color body image 552-4 is an image of the human body 553 oriented in a second side view facing the 2D imaging element. As will be appreciated, any number of 2D color body images 552-1 through 552-N may be generated with the view of the human body 553 in any number or orientations with respect to the 2D imaging element.

Each of the 2D color body images 552-1 through 552-N are processed to segment pixels of the image that represent the human body 553 from pixels of the image that do not represent the human body to produce a silhouette 554 of the human body as represented in that image. Segmentation may be done through, for example, background subtraction, semantic segmentation, etc. In one example, a baseline image of the background may be known and used to subtract out pixels of the image that correspond to pixels of the baseline image, thereby leaving only foreground pixels that represent the human body. The background pixels may be assigned RGB color values for black (i.e., 0,0,0). The remaining pixels may be assigned RGB values for white (i.e., 255, 255, 255) to produce the silhouette 554 or binary segmentation of the human body.

In another example, a CNN utilizing a semantic segmentation algorithm may be trained using images of human bodies or simulated human bodies to train the CNN to distinguish between pixels that represent human bodies and pixels that do not represent human bodies. In such an example, the CNN may process the image 552 and indicate or label pixels that represent the body 553 (foreground) and pixels that do not represent the body (background). The background pixels may be assigned RGB color values for black (i.e., 0,0,0). The remaining pixels may be assigned RGB values for white (i.e., 255, 255, 255) to produce the silhouette 554 or binary segmentation of the human body.

In other implementations, other forms or algorithms, such as edge detection, shape detection, etc., may be used to determine pixels of the image 552 that represent the body 553 and pixels of the image 552 that do not represent the body and a silhouette 554 of the body produced therefrom.

Returning to FIG. 5B, the first 2D color body image 552-1 is processed to segment a plurality of pixels of the first 2D color body image 552-1 that represent the human body 553 from a plurality of pixels of the first 2D color body image 552-1 that do not represent the human body, to produce a front silhouette 554-1 of the human body. The second 2D color body image 552-2 is processed to segment a plurality of pixels of the second 2D color body image 552-2 that represent the human body 553 from a plurality of pixels of the second 2D color body image 552-2 that do not represent the human body, to produce a first side silhouette 554-2 of the human body. The third 2D color body image 552-3 is processed to segment a plurality of pixels of the third 2D color body image 552-3 that represent the human body 553 from a plurality of pixels of the third 2D color body image 552-3 that do not represent the human body, to produce a back silhouette 554-3 of the human body. The fourth 2D color body image 552-4 is processed to segment a plurality of pixels of the fourth 2D color body image 552-4 that represent the human body 553 from a plurality of pixels of the fourth 2D color body image 552-4 that do not represent the human body, to produce a second side silhouette 554-4 of the human body. Processing of the 2D color body images 552-1 through 552-N to produce silhouettes 554-1 through 554-N from different orientations of the human body 553 may be performed for any number of images 552.

As discussed above with respect to FIG. 4, in some implementations, the silhouette may be segmented into different body segments by processing the pixels of the 2D image to determine a likelihood that the pixel corresponds to a segment label (e.g., hair, upper clothing, lower clothing, head, upper right arm, upper left leg, etc.).

Similar to FIG. 5A, in some implementations, in addition to generating a silhouette 554 from the 2D color body image 552, the silhouette may be normalized in size and centered in the image.

Each silhouette 554 representative of the body 553 may then be processed to determine body traits or features of the human body. For example, different CNNs may be trained using silhouettes of bodies, such as human bodies, from different orientations with known features. In some implementations, different CNNs may be trained for different orientations. For example, a first CNN 556A-1 may be trained to determine front view features from front view silhouettes 554-1. A second CNN 556A-2 may be trained to determine right side features from right side silhouettes 554-2. A third CNN 556A-3 may be trained to determine back view features from back view silhouettes 554-3. A fourth CNN 556A-4 may be trained to determine left side features from left side silhouettes 554-4. Different CNNs 556A-1 through 556A-N may be trained for each of the different orientations of silhouettes 554-1 through 554-N. Alternatively, one CNN may be trained to determine features from any orientation silhouette.

In some implementations, the same or different CNNs may also utilize the 2D color body image 502 as an input to the CNN that is used to generate and determine the body features. For example, the first CNN 556A-1 may be trained to determine front view features based on inputs of the front view silhouettes 554-1 and/or the 2D color body image 552-1. The second CNN 556A-2 may be trained to determine right side features from right side silhouettes 554-2 and/or the right side 2D color body image 552-2. The third CNN 556A-3 may be trained to determine back view features from back view silhouettes 554-3 and/or the back view 2D color body image 552-3. The fourth CNN 556A-4 may be trained to determine left side features from left side silhouettes 554-4 and/or the left side 2D color body image 552-4. Different CNNs 556A-1 through 556A-N may be trained for each of the different orientations of silhouettes 554-1 through 554-N and/or 2D color body images 552-1 through 552-N.

In still other implementations, different CNNs may be trained for each of the silhouettes 554 and the 2D color body images. For example, the first CNN 556A-1 may be trained to determine front view features from the silhouette 554-1 and another front view CNN may be trained to determine front view features from the 2D color body image 552-1. The second CNN 556A-2 may be trained to determine right side view features from the silhouette 554-2 and another right side view CNN may be trained to determine right side view features from the 2D color body image 552-2. The third CNN 556A-3 may be trained to determine back view features from the silhouette 554-3 and another back view CNN may be trained to determine back view features from the 2D color body image 552-3. The fourth CNN 556A-4 may be trained to determine left side view features from the silhouette 554-4 and another left side view CNN may be trained to determine left side view features from the 2D color body image 552-4.

In implementations that utilize multiple images of the body 553 and/or multiple silhouettes 554 to produce multiple sets of features, such as the example illustrated in FIG. 5B, those features may be concatenated CNN 556B and the concatenated features processed together with a CNN to generate a set of personalized body features 557. For example, a CNN may be trained to receive features generated from different silhouettes 554, features generated from different 2D color body images 552, and/or features generated by a CNN that processes both silhouettes 554 and the 2D color body images 552 to produce personalized body features 557. The personalized body features 557 may indicate any aspect or information related to the body 553 represented in the images 552. For example, the personalized body features 557 may indicate 3D joint locations, body volume, shape of the body, pose angles, neural network weights corresponding to the body, etc. In some implementations, the concatenated CNN 556B may be trained to predict hundreds of personalized body features 557 corresponding to the body 553 represented in the images 552.

Utilizing the personalized body features 557, one or more regional body composition CNN(s) 570 may process the features and determine regional body composition values 572 for different regions of the body, as discussed further below. Likewise, a personalized 3D body model of the body is generated based on the personalized body features 557. For example, the personalized body features 557 may be provided to a body model, such as the SCAPE body model, the SMPL body model, etc., and the body model may generate the personalized 3D body model of the body 553 represented in the images 552 based on those personalized body features 557.

In the illustrated example, personalized 3D model refinement 558 may be performed to refine or revise the generated personalized 3D body model to better represent the body 553 represented in the 2D color body images 552. For example, as discussed above, the personalized 3D body model may be compared to the body 553 represented in one or more of the 2D color body images 552 to determine differences between the shape of the body 553 represented in the 2D color body image 552 and the shape of the personalized 3D body model generated from the body features. In some implementations, the personalized 3D body model may be compared to a single image, such as image 552-1. In other implementations, the personalized 3D body model may be compared to each of the 2D color body images 552-1 through 552-N in parallel or sequentially. In still other implementations, one or more 2D model images may be generated from the personalized 3D body model and those 2D model images may be compared to the silhouettes and/or the 2D color body images to determine differences between the 2D model images and the silhouette/2D color body images.

Comparing the personalized 3D body model and/or a 2D model image with a 2D color body image 552 or silhouette 554 may include determining an approximate pose of the body 553 represented in the 2D color body image and adjusting the personalized 3D body model to the approximate pose. The personalized 3D body model or rendered 2D model image may then be overlaid or otherwise compared to the body 553 represented in the 2D color body image 552 and/or represented in the silhouette 554 to determine a difference between the personalized 3D body model image and the 2D color body image/silhouette.

Based on the determined differences between the personalized 3D body model and the body 553 represented in the 2D color body image 552, the silhouette 554 generated from that image may be refined to account for those differences. Alternatively, the body features and/or the personalized 3D body model may be refined to account for those differences.

In some implementations, the generated personalized 3D refinement generated by the 3D model refinement 508, may be provided to the regional body composition CNN(s) 570 as an input that is used to determine regional body compositions for the CNN.

In some implementations, upon completion of personalized 3D model refinement 558, the personalized 3D body model of the body 553 represented in the 2D color body images 552 may be augmented with one or more textures, texture augmentation 562, determined from one or more of the 2D color body images 552-1 through 552-N. For example, the personalized 3D body model may be augmented to have a same or similar color to a skin color of the body 553 represented the 2D color body images 552, clothing or clothing colors represented in the 2D color body images 552 may be used to augment the personalized 3D body model, facial features, hair, hair color, etc., of the body 553 represented in the 2D color body image 552 may be determined and used to augment the personalized 3D body model.

Similar to personalized 3D model refinement, the approximate pose of the body in one of the 2D color body images 552 may be determined and the personalized 3D body model adjusted accordingly so that the texture obtained from that 2D color body image 552 may be aligned and used to augment that portion of the personalized 3D body model. In some implementations, alignment of the personalized 3D body model with the approximate pose of the body 553 may be performed for each 2D color body image 552-1 through 552-N so that texture information or data from the different views of the body 553 represented in the different 2D color body images 552 may be used to augment the different poses of the resulting personalized 3D body model.

The result of the processing illustrated in the transition 550 is a personalized 3D body model 564 or avatar representative of the body of the user, that has been generated from 2D color body images 552 of the body 553 of the user. In addition, determined body dimensions 572 may be presented with the personalized 3D body model, as illustrated above.

Figure 6A:
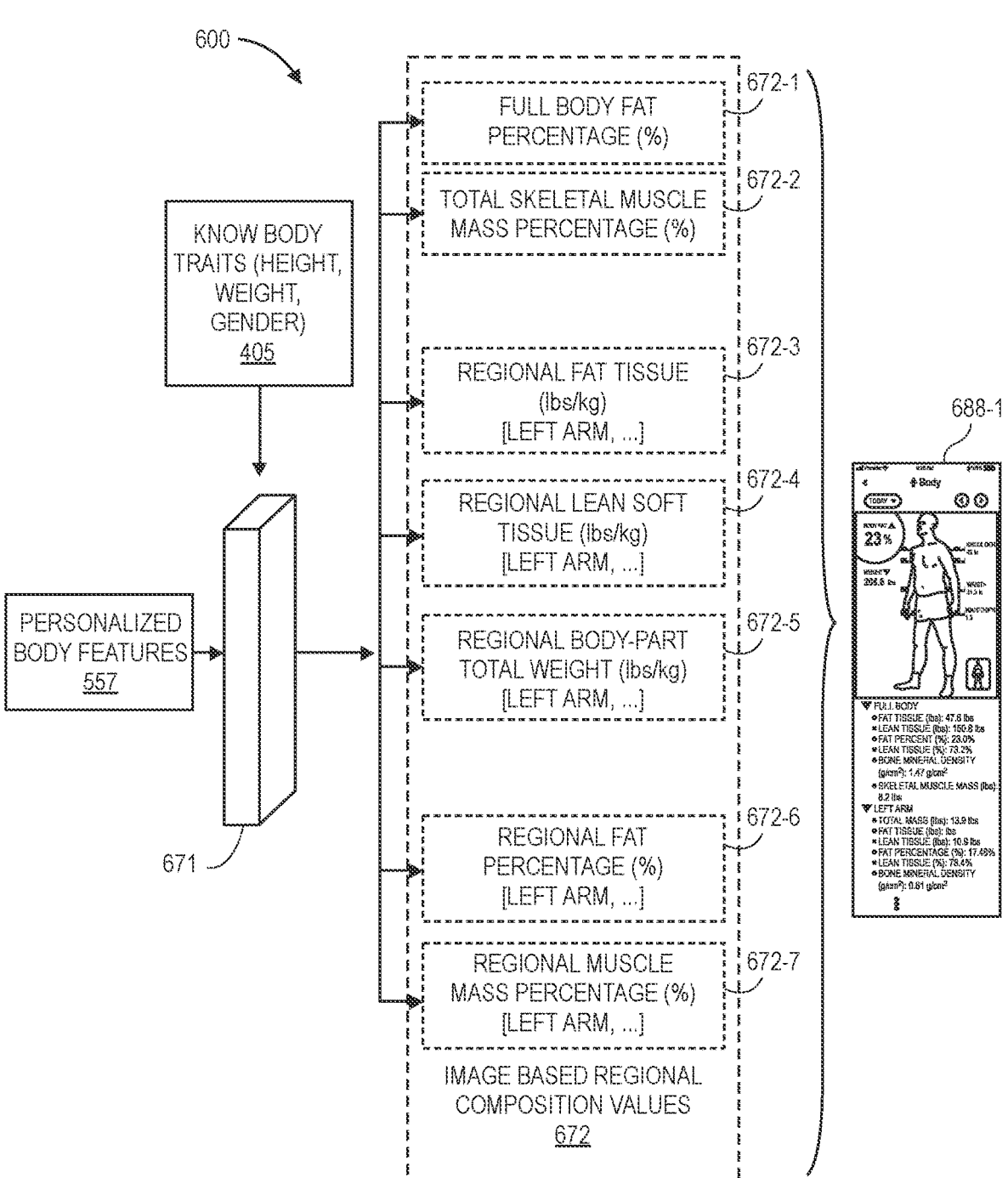
FIG. 6A is a transition diagram indicating additional details for determining regional body composition values of a body based on one or more two-dimensional color body images of the body, in accordance with implementations of the present disclosure.
Figure 6B:
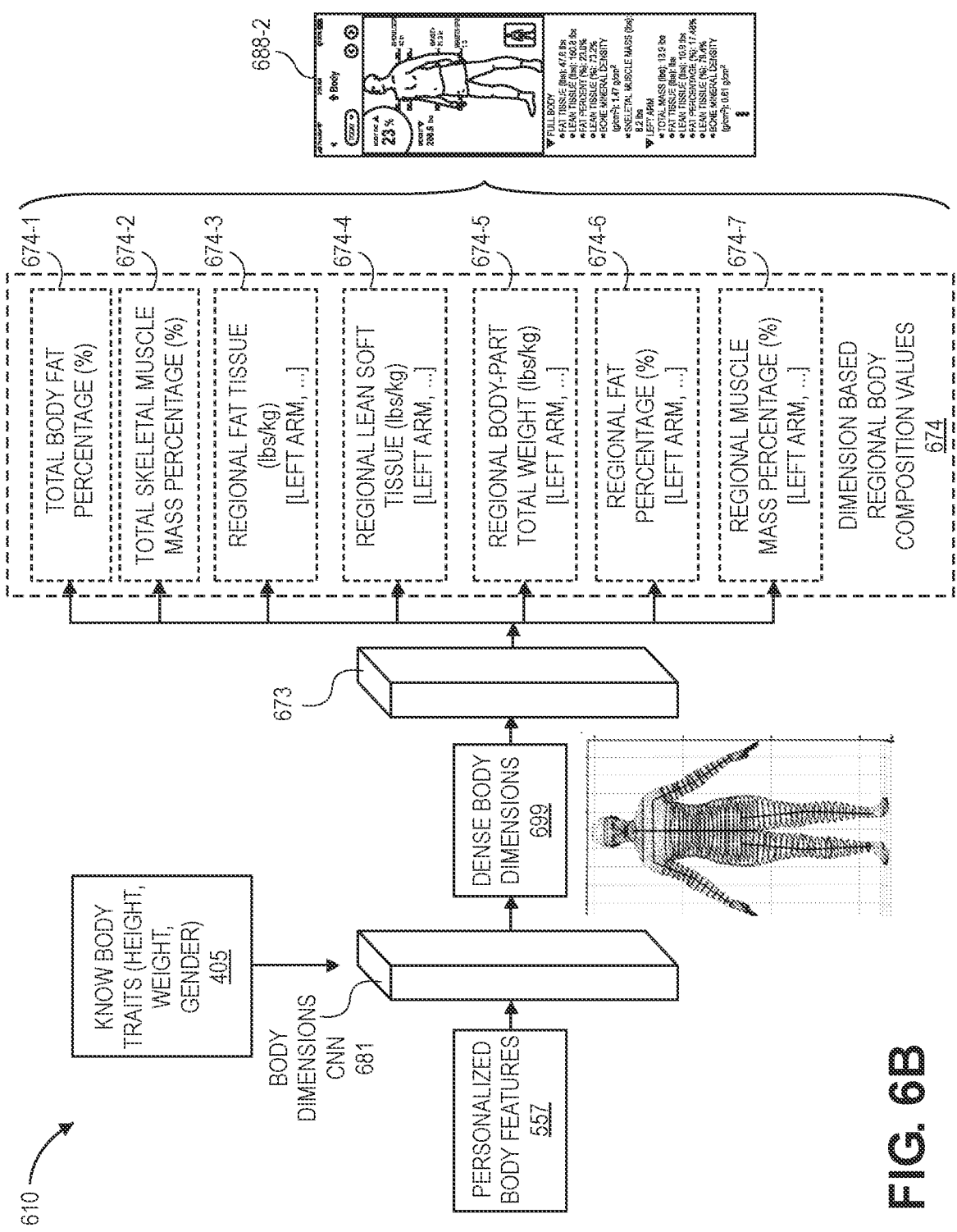
FIG. 6B is another transition diagram indicating additional details for determining regional body composition values of a body based on dense body dimensions determined for the body, in accordance with implementations of the present disclosure.
Figure 6C:
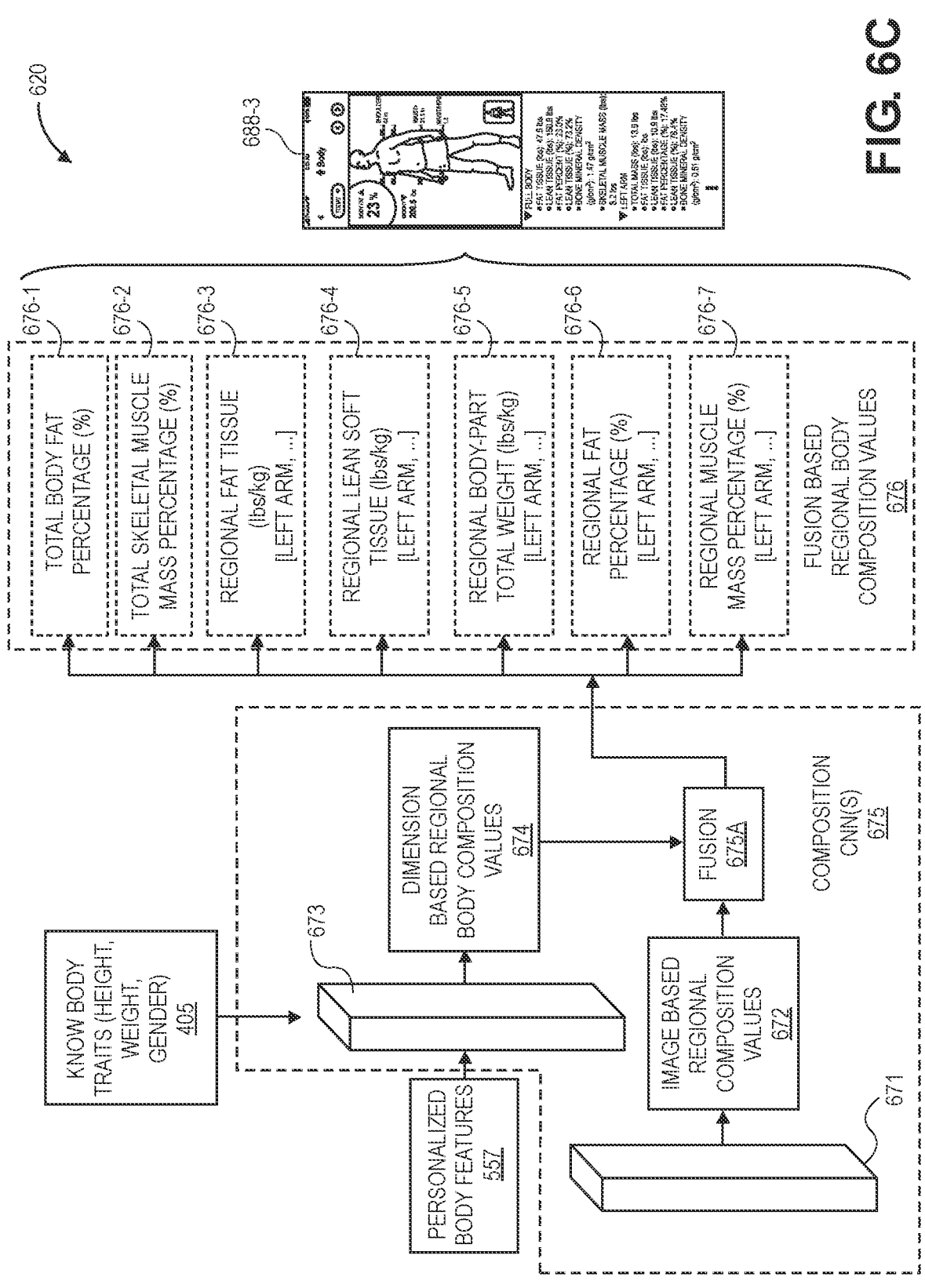
FIG. 6C is another transition diagram indicating additional details for determining regional body composition values of a body based on a fusion of image based body composition values determined with respect to FIG. 6A and dimension based body composition values determined with respect to FIG. 6B, in accordance with implementations of the present disclosure.

FIGS. 6A, 6B, and 6C illustrate transition diagrams indicating additional details for determining regional body composition values of a body represented in one or more 2D color body images. As discussed below, FIG. 6A describes a regional body composition CNN that is trained to receive as inputs, personalized body features generated from one or more 2D images of the body and generate as outputs, regional body composition values, referred to in these examples as image based regional body composition values. FIG. 6B describes a regional body composition CNN that is trained to receive as inputs, body dimension measurements (e.g., circumference measurements) generated from one or more 2D images of the body and generate as outputs, regional body composition values, referred to in these examples as dimension based regional body composition values. FIG. 6C describes a regional body composition CNN that is trained to receive as inputs, image based regional body composition values and dimension based regional body composition values, combine those values, and generate as outputs, regional body composition values, referred to in these examples as fusion based regional body composition values.

Turning first to FIG. 6A, illustrated is a transition diagram 600 indicating additional details for determining image based regional body composition values of a body based on one or more two-dimensional color body images of the body, in accordance with implementations of the present disclosure.

As discussed above, the image based regional body composition CNN(s) 671 receive personalized body features 557 determined for a body represented in one or more 2D images of the body. In some implementations, a single image based regional body composition CNN 671 may receive body features resulting from a concatenation of body features determined from a plurality of 2D color body images of the body taken from different body poses. In other implementations, multiple image based regional body composition CNNs 671 may be utilized, each receiving body features determined from a 2D color body image of the body for different poses of the body. In addition, in some implementations, the image based regional body composition CNNs 671 may receive known body traits, such as the height of the body, the weight of the body, the gender of the body, etc. Alternatively, or in addition thereto, the known body traits of the body may be utilized to generate the personalized body features that are received by the image based regional body composition CNN 671.

In response to receiving the personalized body features 557 and optionally one or more known body traits 405, the image based regional body composition CNN(s) determine a plurality of regional body composition values for different regions of the body. In the illustrated example, the image based regional body composition CNN(s) 671 generate and output as regional body composition values for a body represented in a 2D image, a full body fat percentage 672-1, a total skeletal muscle mass percentage 672-2, regional fat tissue mass 672-3 for different regions of the body (e.g., left arm, right arm, left leg, right leg, torso, etc.), regional lean soft tissue mass 672-4 for different regions of the body (e.g., left arm, right arm, left leg, right leg, torso, etc.), regional body-part total weight 672-5 for different regions of the body (e.g., left arm, right arm, left leg, right leg, torso, etc.), regional fat percentage 672-6 for different regions of the body (e.g., left arm, right arm, left leg, right leg, torso, etc.), and regional muscle mass percentage 672-7 for different regions of the body (e.g., left arm, right arm, left leg, right leg, torso, etc.). As discussed above, any number of regional body composition values 672 may be generated for any number of different regions of a body represented in a 2D image and the ones provided with respect to FIG. 6A are for explanation purposes only.

As discussed above, one or more of the regional body composition values, in this example image based regional body composition values 672 determined for the body may be presented on a device, such as a portable device. For example, the output 688-1 illustrates one or more of the regional body composition values presented concurrent with the 3D body model generated for the body represented in the received 2D image.

FIG. 6B is another transition diagram 610 indicating additional details for determining dimension based regional body composition values of a body based on dense body dimensions 699 determined for a body represented in a 2D image, in accordance with implementations of the present disclosure.

In the example illustrated in FIG. 6B, a body dimensions CNN 681, that is trained to process personalized body features 557 and output dense body dimensions 699 for the body represented in a 2D image may be utilized. Dense body dimensions include, but are not limited to circumference measurements, such as bicep circumference, neck circumference, waist circumference, hip circumference, chest circumference, forearm circumference, upper leg circumference, lower leg circumference, shoulder circumference to hip circumference ratio, etc.

The body dimension CNN 681 may receive personalized body features 557 determined for a body represented in one or more 2D images of the body. In some implementations, a single body dimensions CNN 681 may receive body features resulting from a concatenation of body features determined from a plurality of 2D color body images of the body taken from different body poses. In other implementations, multiple body dimension CNNs 681 may be utilized, each receiving body features determined from a 2D color body image of the body for different poses of the body. In addition, in some implementations, the body dimensions CNNs 681 may receive known body traits 405, such as the height of the body, the weight of the body, the gender of the body, etc. Alternatively, or in addition thereto, the known body traits 405 of the body may be utilized to generate the personalized body features 557 that are received by the dimension based regional body composition CNN 673.

In response to receiving the personalized body features 557 and optionally the known body traits 405, the body dimensions CNN(s) 681 determine a plurality of body dimensions 699 for different regions or segments of the body, collectively referred to herein as dense body dimension values or dense body dimensions 699. In some implementations, body dimension values (e.g., circumference values) may be generated for each region of the body for which the regional body dimension CNN(s) 681 is trained to output regional body composition values. In other implementations, multiple body dimension values for each region of the body may be determined by the body dimension CNN(s) 681.

The dense body dimension values 699 output by the body dimension CNN(s) 681 are provided to a dimension based regional body composition CNN 673 and the dimension based regional body composition CNN 673, in response to receiving the dense body dimensions 699, determines a plurality of dimension based regional body composition values 674 for different regions of the body. In the illustrated example, the dimension based regional body composition CNN(s) 673 generate and output as dimension based regional body composition values for a body represented in a 2D image a total body fat percentage 674-1, a total skeletal muscle mass percentage 674-2, regional fat tissue mass 674-3 for different regions of the body (e.g., left arm, right arm, left leg, right leg, torso, etc.), regional lean soft tissue mass 674-4 for different regions of the body (e.g., left arm, right arm, left leg, right leg, torso, etc.), regional body-part total weight 674-5 for different regions of the body (e.g., left arm, right arm, left leg, right leg, torso, etc.), regional fat percentage 674-6 for different regions of the body (e.g., left arm, right arm, left leg, right leg, torso, etc.), and regional muscle mass percentage 674-7 for different regions of the body (e.g., left arm, right arm, left leg, right leg, torso, etc.). As discussed above, any number of regional body composition values may be generated for any number of different regions of a body represented in a 2D image and the ones provided with respect to FIG. 6B are for explanation purposes only.

As discussed above, one or more of the regional body composition values, in this example dimension based regional body composition values 674 determined for the body may be presented on a device, such as a portable device. For example, the output 688-2 illustrates one or more of the regional body composition values presented concurrent with the 3D body model generated for the body represented in the received 2D image.

FIG. 6C is another transition diagram 620 indicating additional details for determining fusion based regional body composition values 676 of a body based on a fusion of image based regional body composition values 672 determined with respect to FIG. 6A and dimension based regional body composition values 674 determined with respect to FIG. 6B, in accordance with implementations of the present disclosure.

In the example discussed with respect to FIG. 6C a fusion component 675A, which may be another trained CNN, an algorithm, a rule based process, or computing system executing a fusion based regional body composition generation process, such as the fusion based regional body composition generation process 1400 discussed below with respect to FIG. 14, may receive as inputs, the image based regional body composition values 672 and the dimension based regional body composition values 674 generated by the image based regional body composition CNN(s) 671 and the dimension based regional body composition CNN(s) 673, respectively.

As discussed further below; the image based regional body composition values 672 and the dimension based regional body composition values 674 may be combined at the fusion component 675A to generate fusion based regional body composition values 676. In some implementations, an average of each respective image based regional body composition value 672 and each dimension based regional body composition value 674 may be utilized to generate a fusion based regional body composition value 676. In other examples, one or more weightings may be applied to either or both of the image based regional body composition values 672 and/or the dimension based regional body composition values 674 as part of determining the fusion based regional body composition values 676.

Similar to FIGS. 6A and 6B, in the illustrated example, the fusion based regional body composition CNN(s) 675 generates and outputs as fusion based regional body composition values 676 for a body represented in a 2D image a total body fat percentage 676-1, a total skeletal muscle mass percentage 676-2, regional fat tissue mass 676-3 for different regions of the body (e.g., left arm, right arm, left leg, right leg, torso, etc.), regional lean soft tissue mass 676-4 for different regions of the body (e.g., left arm, right arm, left leg, right leg, torso, etc.), regional body-part total weight 676-5 for different regions of the body (e.g., left arm, right arm, left leg, right leg, torso, etc.), regional fat percentage 676-6 for different regions of the body (e.g., left arm, right arm, left leg, right leg, torso, etc.), and regional muscle mass percentage 676-7 for different regions of the body (e.g., left arm, right arm, left leg, right leg, torso, etc.). As discussed above, any number of regional body composition values may be generated for any number of different regions of a body represented in a 2D image and the ones provided with respect to FIG. 6C are for explanation purposes only.

As discussed above, one or more of the regional body composition values, in this example fusion based regional body composition values 676 determined for the body may be presented on a device, such as a portable device. For example, the output 688-3 illustrates one or more of the regional body composition values presented concurrent with the 3D body model generated for the body represented in the received 2D image.

While the above examples discussed with respect to FIGS. 6A, 6B, and 6C distinguish between an image based regional body composition CNN 671, a dimension based regional body composition CNN 673, and fusion based regional body composition CNN 675, unless specifically indicated otherwise, each of the image based regional body composition CNN 671, dimension based regional body composition CNN 673, and fusion based regional body composition CNN 675 may be generally referred to as a regional body composition CNN. Likewise, the fusion based regional body composition CNN 675 may collectively include each of the image based regional body composition CNN 671, the dimension based regional body composition CNN 673, and the fusion component 675A. Still further, while the above examples discussed with respect to FIGS. 6A, 6B, and 6C distinguish between image based regional body composition values 672, a dimension based regional body composition values 674, and fusion based regional body composition values 676, unless specifically indicated otherwise, each of the image based regional body composition values 672, dimension based regional body composition values 674, and fusion based regional body composition values 676 may be generally referred to as a regional body composition values.

Figure 7:
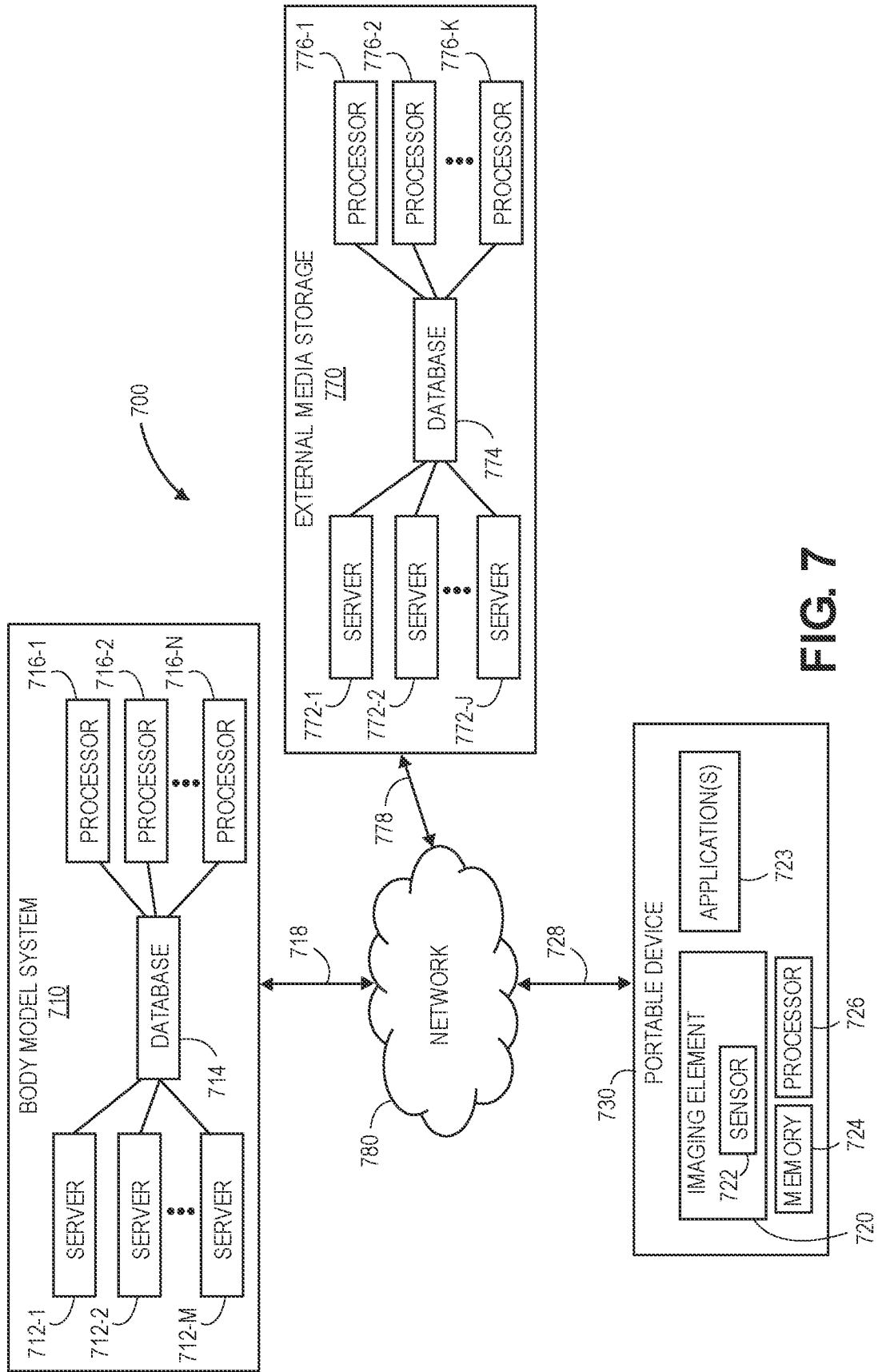
FIG. 7 is a block diagram of components of an image processing system, in accordance with implementations of the present disclosure.

Referring to FIG. 7, a block diagram of components of one image processing system 700 in accordance with implementations of the present disclosure is shown.

The system 700 of FIG. 7 includes a body model system 710, an imaging element 720 that is part of a portable device 730 of a user, such as a tablet, a laptop, a cellular phone, a webcam, etc., and an external media storage facility 770 connected to one another across a network 780, such as the Internet.

The body model system 710 of FIG. 7 includes M physical computer servers 712-1, 712-2 . . . 712-M having one or more databases (or data stores) 714 associated therewith, as well as N computer processors 716-1, 716-2 . . . 716-N provided for any specific or general purpose. For example, the body model system 710 of FIG. 7 may be independently provided for the exclusive purpose of generating personalized 3D body models, body dimensions, and/or regional based body composition values from 2D color body images captured by imaging elements, such as imaging element 720, or silhouettes produced therefrom, or alternatively, provided in connection with one or more physical or virtual services configured to manage or monitor such information, as well as one or more other functions. The servers 712-1, 712-2 . . . 712-M may be connected to, or otherwise communicate with the databases 714 and the processors 716-1, 716-2 . . . 716-N. The databases 714 may store any type of information or data, including simulated silhouettes, body features, simulated 3D body models, etc.

The servers 712-1, 712-2 . . . 712-M and/or the computer processors 716-1, 716-2 . . . 716-N may also connect to, or otherwise communicate with the network 780, as indicated by line 718, through the sending and receiving of digital data.

The imaging element 720 may comprise any form of optical recording sensor or device that may be used to photograph or otherwise record information or data regarding a body of the user, or for any other purpose. As is shown in FIG. 7, the portable device 730 that includes the imaging element 720 is connected to the network 780 and includes one or more sensors 722, one or more memory or storage components 724 (e.g., a database or another data store), one or more processors 726, and any other components that may be required in order to capture, analyze and/or store imaging data, such as the 2D color body images discussed herein. For example, the imaging element 720 may capture one or more still or moving images and may also connect to, or otherwise communicate with the network 780, as indicated by the line 728, through the sending and receiving of digital data. Although the system 700 shown in FIG. 7 includes just one imaging element 720 therein, any number or type of imaging elements, portable devices, or sensors may be provided within any number of environments in accordance with the present disclosure.

The portable device 730 may be used in any location and any environment to generate 2D color body images that represent a body of the user. In some implementations, the portable device may be positioned such that it is stationary and approximately vertical (within approximately ten-degrees of vertical) and the user may position their body within a field of view of the imaging element 720 of the portable device 730 at different orientations so that the imaging element 720 of the portable device may generate 2D color body images that include a representation of the body of the user from different orientations.

The portable device 730 may also include one or more applications 723 stored in memory that may be executed by the processor 726 of the portable device to cause the processor of the portable device to perform various functions or actions. For example, when executed, the application 723 may provide instructions to a user regarding placement of the portable device 730, positioning of the body of the user within the field of view of the imaging element 720 of the portable device, orientation of the body of the user, etc. Likewise, in some implementations, the application 723 may present a personalized 3D body model, regional body composition values, and/or body dimensions determined and generated from the 2D color body images in accordance with the described implementations, to the user and allow the user to interact with the personalized 3D body model. For example, a user may rotate the personalized 3D body model to view different angles of the personalized 3D body model, view accurate regional body composition values and/or body dimensions determined from the 2D images, etc.

The external media storage facility 770 may be any facility, station or location having the ability or capacity to receive and store information or data, such as silhouettes, simulated or rendered personalized 3D body models of bodies, textures, body dimensions, regional body composition values, etc., received from the body model system 710, and/or from the portable device 730. As is shown in FIG. 7, the external media storage facility 770 includes J physical computer servers 772-1, 772-2 . . . 772-J having one or more databases 774 associated therewith, as well as K computer processors 776-1, 776-2 . . . 776-K. The servers 772-1, 772-2

. . . 772-J may be connected to, or otherwise communicate with the databases 774 and the processors 776-1, 776-2 . . . 776-K. The databases 774 may store any type of information or data, including digital images, silhouettes, personalized 3D body models, etc. The servers 772-1, 772-2 . . . 772-J and/or the computer processors 776-1, 776-2 . . . 776-K may also connect to, or otherwise communicate with the network 780, as indicated by line 778, through the sending and receiving of digital data.

The network 780 may be any wired network, wireless network, or combination thereof, and may comprise the Internet in whole or in part. In addition, the network 780 may be a personal area network, local area network, wide area network, cable network, satellite network, cellular telephone network, or combination thereof. The network 780 may also be a publicly accessible network of linked networks, possibly operated by various distinct parties, such as the Internet. In some implementations, the network 780 may be a private or semi-private network, such as a corporate or university intranet. The network 780 may include one or more wireless networks, such as a Global System for Mobile Communications (GSM) network, a Code Division Multiple Access (CDMA) network, a Long Term Evolution (LTE) network, or some other type of wireless network. Protocols and components for communicating via the Internet or any of the other aforementioned types of communication networks are well known to those skilled in the art of computer communications and thus, need not be described in more detail herein.

The computers, servers, devices and the like described herein have the necessary electronics, software, memory, storage, databases, firmware, logic/state machines, microprocessors, communication links, displays or other visual or audio user interfaces, printing devices, and any other input/output interfaces to provide any of the functions or services described herein and/or achieve the results described herein. Also, those of ordinary skill in the pertinent art will recognize that users of such computers, servers, devices and the like may operate a keyboard, keypad, mouse, stylus, touch screen, or other device (not shown) or method to interact with the computers, servers, devices and the like, or to "select" an item, link, node, hub or any other aspect of the present disclosure.

The body model system 710, the portable device 730 or the external media storage facility 770 may use any web-enabled or Internet applications or features, or any other client-server applications or features including E-mail or other messaging techniques, to connect to the network 780, or to communicate with one another, such as through short or multimedia messaging service (SMS or MMS) text messages. For example, the servers 712-1, 712-2 . . . 712-M may be adapted to transmit information or data in the form of synchronous or asynchronous messages from the body model system 710 to the processor 726 or other components of the portable device 730, or any other computer device in real time or in near-real time, or in one or more offline processes, via the network 780. Those of ordinary skill in the pertinent art would recognize that the body model system 710, the portable device 730 or the external media storage facility 770 may operate any of a number of computing devices that are capable of communicating over the network, including but not limited to set-top boxes, personal digital assistants, digital media players, web pads, laptop computers, desktop computers, electronic book readers, cellular phones, and the like. The protocols and components for providing communication between such devices are well known to those skilled in the art of computer communications and need not be described in more detail herein.

The data and/or computer executable instructions, programs, firmware, software and the like (also referred to herein as "computer executable" components) described herein may be stored on a computer-readable medium that is within or accessible by computers or computer components such as the servers 712-1, 712-2 . . . 712-M, the processor 726, the servers 772-1, 772-2 . . . 772-J, or any other computers or control systems utilized by the body model system 710, the portable device 730, applications 723, or the external media storage facility 770, and having sequences of instructions which, when executed by a processor (e.g., a central processing unit, or "CPU"), cause the processor to perform all or a portion of the functions, services and/or methods described herein. Such computer executable instructions, programs, software and the like may be loaded into the memory of one or more computers using a drive mechanism associated with the computer-readable medium, such as a floppy drive, CD-ROM drive, DVD-ROM drive, network interface, or the like, or via external connections.

Some implementations of the systems and methods of the present disclosure may also be provided as a computer-executable program product including a non-transitory machine-readable storage medium having stored thereon instructions (in compressed or uncompressed form) that may be used to program a computer (or other electronic device) to perform processes or methods described herein. The machine-readable storage media of the present disclosure may include, but is not limited to, hard drives, floppy diskettes, optical disks, CD-ROMs, DVDs, ROMs, RAMs, erasable programmable ROMs ("EPROM"), electrically erasable programmable ROMs ("EEPROM"), flash memory, magnetic or optical cards, solid-state memory devices, or other types of media/machine-readable medium that may be suitable for storing electronic instructions. Further, implementations may also be provided as a computer executable program product that includes a transitory machine-readable signal (in compressed or uncompressed form). Examples of machine-readable signals, whether modulated using a carrier or not, may include, but are not limited to, signals that a computer system or machine hosting or running a computer program can be configured to access, or including signals that may be downloaded through the Internet or other networks.

As discussed above, features or objects expressed in imaging data, such as human bodies, colors, textures or outlines of the features or objects, may be extracted from the data in any number of ways. For example, colors of pixels, or of groups of pixels, in a digital image may be determined and quantified according to one or more standards, e.g., the RGB color model, in which the portions of red, green or blue in a pixel are expressed in three corresponding numbers ranging from 0 to 255 in value, or a hexadecimal model, in which a color of a pixel is expressed in a six-character code, wherein each of the characters may have a range of sixteen. Moreover, textures or features of objects expressed in a digital image may be identified using one or more computer-based methods, such as by identifying changes in intensities within regions or sectors of the image, or by defining areas of an image corresponding to specific surfaces.

Furthermore, edges, contours, outlines, colors, textures, silhouettes, shapes or other characteristics of objects, or portions of objects, expressed in images may be identified using one or more algorithms or machine-learning tools. The objects or portions of objects may be identified at single, finite periods of time, or over one or more periods or durations. Such algorithms or tools may be directed to recognizing and marking transitions (e.g., the edges, contours, outlines, colors, textures, silhouettes, shapes or other characteristics of objects or portions thereof) within the digital images as closely as possible, and in a manner that minimizes noise and disruptions, and does not create false transitions. Some detection algorithms or techniques that may be utilized in order to recognize characteristics of objects or portions thereof in digital images in accordance with the present disclosure include, but are not limited to, Canny edge detectors or algorithms: Sobel operators, algorithms or filters; Kayyali operators: Roberts edge detection algorithms: Prewitt operators: Frei-Chen methods; semantic segmentation algorithms: background subtraction: or any other algorithms or techniques that may be known to those of ordinary skill in the pertinent arts.

Image processing algorithms, other machine learning algorithms or CNNs may be operated on computer devices of various sizes or types, including but not limited to smartphones or other cell phones, tablets, video cameras or other computer-based machines. Such mobile devices may have limited available computer resources, e.g., network bandwidth, storage capacity or processing power, as compared to larger or more complex computer devices. Therefore, executing computer vision algorithms, other machine learning algorithms, or CNNs on such devices may occupy all or much of the available resources, without any guarantee, or even a reasonable assurance, that the execution of such algorithms will be successful. For example, processing digital 2D color body images captured by a user of a portable device (e.g., smartphone, tablet, laptop, webcam) according to one or more algorithms in order to produce a personalized 3D body model from the digital images may be an ineffective use of the limited resources that are available on the smartphone or tablet. Accordingly, in some implementations, as discussed herein, some or all of the processing may be performed by one or more computing resources that are remote from the portable device. In some implementations, initial processing of the images to generate binary segmented silhouettes may be performed on the device. Subsequent processing to generate and refine the personalized 3D body model may be performed on one or more remote computing resources. For example, the silhouettes may be sent from the portable device to the remote computing resources for further processing. Still further, in some implementations, texture augmentation of the personalized 3D body model of the body may be performed on the portable device or remotely. Likewise, the determination of regional body composition values maybe determined on the portable device, remotely, or partially determined on the portable device and partially determined remotely.

In some implementations, to increase privacy of the user, only the binary segmented silhouette, personalized body features, and/or body dimensions may be sent from the device for processing on the remote computing resources and the original 2D images that include the representation of the user may be maintained locally on the portable device. In such an example, the rendered personalized 3D body model and regional body composition values may be sent back to the device and the device may perform texture augmentation of the received personalized 3D body model based on those images. Utilizing such a distributed computing arrangement retains user identifiable information on the portable device of the user while at the same time leveraging the increased computing capacity available at remote computing resources.

Machine learning tools, such as artificial neural networks, have been utilized to identify relations between respective elements of apparently unrelated sets of data. An artificial neural network, such as a CNN, is a parallel distributed computing processor comprised of individual units that may collectively learn and store experimental knowledge, and make such knowledge available for use in one or more applications. Such a network may include multiple layers that acquire knowledge from an environment through one or more flexible learning processes, determining the strengths of the respective connections between such layers, and utilizing such strengths when storing acquired knowledge. An artificial neural network may use any number of layers, including an input layer, an output layer, and one or more intervening hidden layers. In view of their versatility, machine learning tools including not only artificial neural networks but also nearest neighbor methods or analyses, factorization methods or techniques, K-means clustering analyses or techniques, similarity measures such as log likelihood similarities or cosine similarities, latent Dirichlet allocations or other topic models, or latent semantic analyses have been utilized in image processing applications.

The training of a neural network is typically characterized as supervised, semi-supervised, or unsupervised. In supervised learning, a training set comprises at least one input and at least one target output or label for the input. Thus, the neural network is trained to identify the target output(s), to within an acceptable level of error. In semi-supervised learning, such as a teacher-student training model, initial training is performed with labeled training data to initially train the model or set of models, such as a set of teacher models. The initially trained models may then further process unlabeled training data and a consensus of the outputs from the initially trained, or teacher models, may be utilized to generate a fully trained model or student models.

In unsupervised learning of an identity function, such as that which is typically performed by a sparse autoencoder, target output of the training set is the input, and the neural network is trained to recognize the input as such. Sparse autoencoders employ backpropagation in order to train the autoencoders to recognize an approximation of an identity function for an input, or to otherwise approximate the input. Such backpropagation algorithms may operate according to methods of steepest descent, conjugate gradient methods, or other like methods or techniques, in accordance with the systems and methods of the present disclosure. Those of ordinary skill in the pertinent art would recognize that any algorithm or method may be used to train one or more layers of a neural network. Likewise, any algorithm or method may be used to determine and minimize the error in an output of such a network. Additionally, those of ordinary skill in the pertinent art would further recognize that the various layers of a neural network may be trained collectively, such as in a sparse autoencoder, or individually, such that each output from one hidden layer of the neural network acts as an input to a subsequent hidden layer.

Once a neural network has been trained to recognize dominant characteristics of an input of a training set, e.g., to associate an image with a label, a category, a cluster or a pseudo-label thereof, to within an acceptable tolerance, an input and/or multiple inputs, in the form of an image, silhouette, features, known traits corresponding to the image, etc., may be provided to the trained network, and one or more outputs generated therefrom. For example, the CNN discussed above may receive as inputs a generated silhouette and one or more known body traits (e.g., height, weight, gender) corresponding to the body represented by the silhouette. The trained CNN may then produce as outputs the predicted features corresponding to those inputs.

FIG. 8A is an example regional body composition model training process 800, in accordance with implementations of the present disclosure. The example process 800 may be used to train a neural network to generate regional body composition values for a plurality of regions of a body, such as a human body, represented in one or more 2D images.

The example process 800 begins by obtaining a group of existing body scans and/or 2D color body images along with regional body composition values for the body represented in the body scan/2D color body images, as in 802. Existing body scans may include, but are not limited to, body scans provided by users, public databases of body scans with corresponding regional body composition values, etc. Likewise, the obtained 2D color body images may be any 2D color body images of a body along with corresponding regional body composition values. In general, the only requirement for the obtained body scans/2D images and corresponding regional body composition values is that the body scans and/or 2D color body images may be processed as discussed above to generate personalized body features corresponding to the body and that the regional body composition values correspond to the body represented in the body scan/2D color body image. Alternatively, or in addition to receiving body scans/2D color body images, the example process may receive personalized body features and corresponding regional body composition values. In such an example, processing of the body scan or 2D color body images to generate personalized body features may be omitted from the example training process 800. In some implementations, the labeled training data may be a limited set of data, such as 5,000-10,000 pairs of information (personalized body features and corresponding regional body composition values).

The labeled training data may then be utilized to train an initial number ("N") of deep neural networks ("DNNs"), such as a CNN, to receive personalized body features determined from the body scans and to output the regional body composition values for which the DNN is trained, referred to herein as teacher models, as in 804. Training of the N number of teacher models using the labeled training data may be performed using typical machine learning training techniques utilized with supervised learning and need not be discussed in detail herein.

Once training of the N number of teacher models has been completed, an unlabeled set of training data may be obtained, as in 806. The unlabeled training data may be, for example, a set of 2D color body images, synthetically generated 2D color body images (as discussed below), or a combination of 2D color body images and synthetically generated 2D color body images.

The training data set may then be processed by each of the N number of trained teacher models and outputs generated by each of the N number of teacher models indicating the regional body composition values determined for each color body image of the training data set, as in 808. The outputs for each regional body composition value for each color body image generated by each of the N number of teacher models may then be combined or a consensus determined and utilized to generate or train a regional body composition model, also referred to herein as a student model. For example, the outputs of the N number of trained teacher models for the color body images included in the training data set may be combined to determine regional body composition values for each color body image and utilized as labels for those images, thereby generated labeled training data that is used to train the regional body composition model (student model). Combining of the outputs from the N number of teacher models may include any one or more of averaging the outputs of the N number of teacher models, selecting the median output of the N number of teacher models, selecting a value that is determined by a majority or most frequently by the N number of teacher models, a weighted combination of the teacher output values, etc.

Upon generating the labeled training data set based on the consensus of the N number of teacher model outputs of the data included in the training data set, the regional body composition model may be trained as if the training data set is labeled training data using typical supervised learning techniques, as in 810.

Figure 8B:
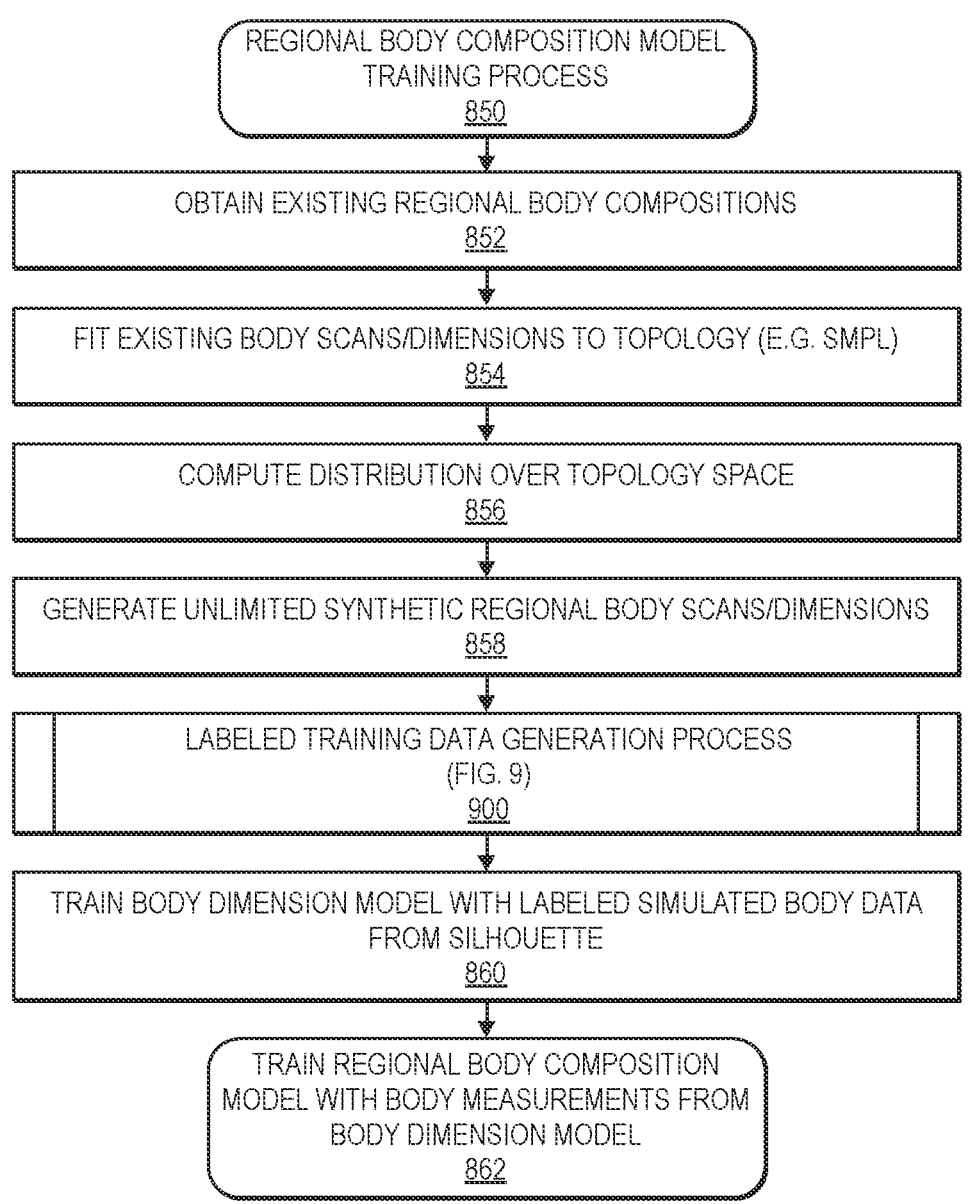
FIG. 8B is another example regional body composition model training process, in accordance with implementations of the present disclosure.

FIG. 8B is another example regional body composition model training process 850, in accordance with implementations of the present disclosure. The example process 850 may be used to generate labeled simulated data that is used to train a neural network, such as a CNN, to determine regional body compositions from a silhouette of a body, such as a human body, as discussed herein.

The example process 850 begins by obtaining existing body scans/regional body composition values of a group of bodies, as in 852. Existing body scans may include, but are not limited to, body scans provided by users, public databases of regional body composition values and corresponding 3D body scans, etc. In general, the only requirement for the existing body scans and regional body composition values be that the regional body composition values include some or all of the regional body composition values for which the regional body composition model is to be trained. In some implementations, the existing body scan/regional body composition values may be a limited set of data, such as 5,000-10,000 existing body scans/regional body composition values of different bodies of different dimensions.

The existing body scans/regional body composition values may then be fit to a topology, such as SMPL model, or other similar topology, as in 854. Using the topology and the different regional body composition values corresponding to the different body scans, the example process 850 computes a distribution of any number of derivative body scans and corresponding regional body composition values across the topology space, as in 856. For example, the body scans/regional body composition values may be integrated between two existing body scans/regional body composition values to compute essentially an infinite number of additional bodies and corresponding regional body composition values between those two existing body scans and corresponding regional body composition values.

Utilizing the computed distribution, an unlimited number of synthetic 3D body models and corresponding regional body composition values may then be generated, as in 858. For example, the initial set of 5,000-10,000 existing body scans and corresponding regional body composition values may be expanded to include hundreds of thousands, millions, or more 3D body models and corresponding regional body composition values of varying sizes and shapes for which the regional body composition values and synthetic body model are known.

The synthetic 3D body model and corresponding regional body composition values may then be used to generate labeled simulated body data using the labeled training data generation process 900, as discussed further below with respect to FIG. 9. The result of the labeled training data generation process 900 (FIG. 9) is labeled simulated body data. As discussed below, the labeled simulated body data includes silhouettes generated from the synthetic 3D body models and the corresponding regional body composition values for that synthetic 3D body model. In other implementations, the labeled simulated body data includes body features representative of the synthetic 3D body model, as determined from one or more silhouettes of that synthetic 3D body model.

Utilizing the labeled simulated body data, a body dimension model may be trained to determine body dimensions values from one or more input color body images, as in 860. Finally, the regional body composition model may be trained to determine regional body composition values based on the outputs from the trained body dimensions model, as discussed herein, as in 862. Training of the regional body composition model may be performed using supervised learning and the labeled simulated body data as the training inputs.

Figure 9:
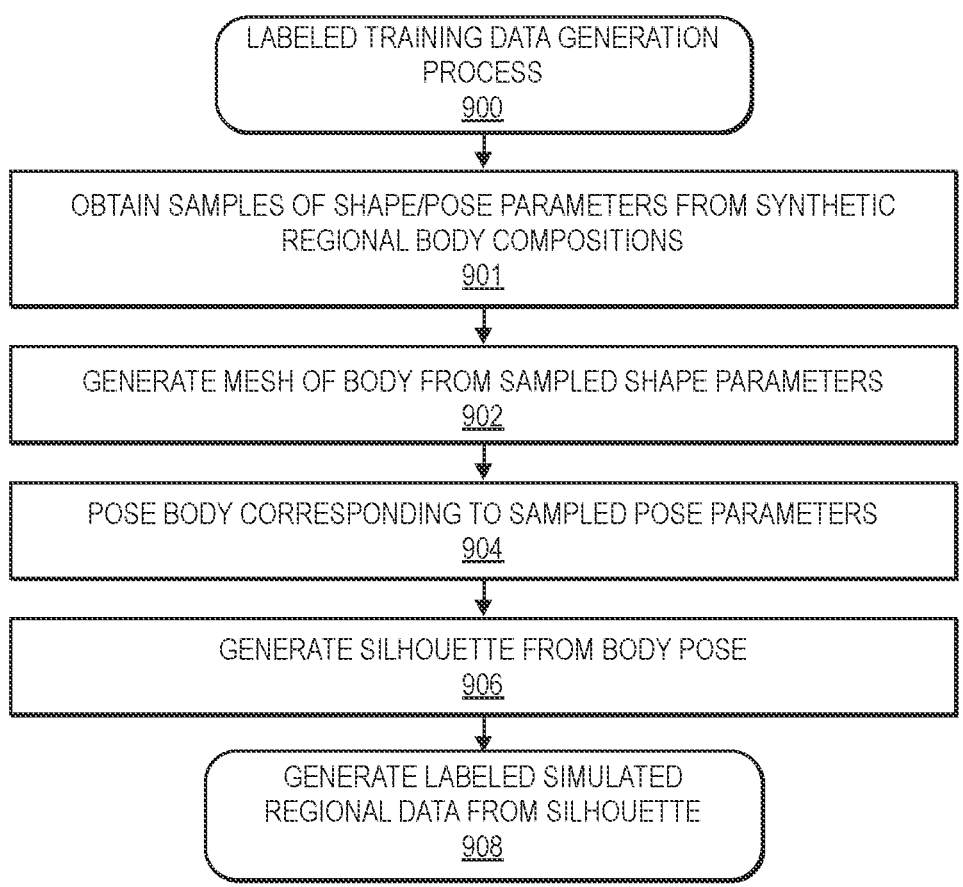
FIG. 9 is an example labeled training data generation process, in accordance with implementations of the present disclosure.

FIG. 9 is an example labeled training data generation process 900, in accordance with implementations of the present disclosure.

The example process 900 begins by obtaining samples of the shape/pose parameters from synthetic body scans and corresponding body dimensions, as in 901. A mesh of a body may then be generated for each sampled shape parameters, as in 902. Generating a mesh of a body may be performed using any of a variety of 3D modeling techniques or engines. For example, any one or more of Blender, OpenGL, Neural Mesh Render, etc., may be used to generate a mesh of a body.

Each mesh of a body may then be positioned to correspond to the obtained sampled pose parameters, as in 904. In some implementations, the position of the mesh may also be varied slightly between body meshes and/or positioned in a defined pose, such as an "A Pose." For example, the orientation, rotation, distance, amount of leg and/or arm separation, etc., may be varied between meshes of bodies, thereby increasing the realistic aspect of the synthetic data.

For each posed mesh of a body, one or more silhouettes are generated, as in 906. For example, multiple silhouettes may be generated from the posed mesh of the body, each silhouette from different orientations (e.g., front view, right side view, back view, left side view; etc.). Generation of a silhouette from a posed mesh of a body may be performed in a manner similar to the discussion above for generating a silhouette from a 2D color body image. For example, a 2D representation of the posed mesh of the body may be generated, thereby indicative of a 2D color body image of a body, and then the 2D representation utilized to generate a silhouette of the posed mesh of the body. In other implementations, the silhouette(s) of the 3D mesh may be determined directly from the posed mesh of the body. In some implementations, body features representative of the posed mesh of the body may be generated from the silhouette(s), as discussed above.

Finally, the silhouette(s) and/or body features determined from the silhouette(s) for each synthetic body may be combined with the regional body composition values generated for that synthetic body to generate labeled simulated body data, as in 908.

FIG. 10 is an example flow diagram of a personalized 3D body model generation process 1000, in accordance with implementations of the present disclosure.

The example process 1000 begins upon receipt of one or more 2D color body images of a body, as in 1002. As noted above, the disclosed implementations are operable with any number of 2D color body images for use in generating a personalized 3D body model of that body. For example, in some implementations, a single 2D color body image may be used. In other implementations, two, three, four, or more 2D color body images may be used.

As discussed above, the 2D color body images may be generated using any 2D imaging element, such as a camera on a portable device, a webcam, etc. The received 2D color body images are then segmented to produce a binary silhouette of the body represented in the one or more 2D color body images, as in 1004. As discussed above, one or more segmentation techniques, such as background subtraction, semantic segmentation, Canny edge detectors or algorithms, Sobel operators, algorithms or filters, Kayyali operators, Roberts edge detection algorithms, Prewitt operators, Frei-Chen methods, or any other algorithms or techniques that may be known to those of ordinary skill in the pertinent arts. In some implementations, the silhouette may be further segmented into body segments.

In addition, in some implementations, the silhouettes may be normalized in height and centered in the image before further processing, as in 1006. For example, the silhouettes may be normalized to a standard height based on a function of a known or provided height of the body of the user represented in the image and an average height (e.g., average height of female body, average height of male body). In some implementations, the average height may be more specific than just gender. For example, the average height may be the average height of a gender and a race corresponding to the body, or a gender and a location (e.g., United States) of the user, etc.

The normalized and centered silhouette may then be processed by one or more neural networks, such as one or more CNNs as discussed above, to generate body parameters representative of the body represented in the 2D color body images, as in 1008. As discussed above, there may be multiple steps involved in body parameter prediction. For example, each silhouette may be processed using CNNs trained for the respective orientation of the silhouette to generate sets of features of the body as determined from the silhouette. The sets of features generated from the different silhouette may then be processed using a neural network, such as a CNN, to concatenate the features and generate the body parameters representative of the body represented in the 2D color body images.

The body parameters may then be provided to one or more body models, such as an SMPL body model or a SCAPE body model and the body model may generate a personalized 3D body model for the body represented in the 2D color body images, as in 1010. In addition, in some implementations, the personalized 3D body model may be refined, if necessary, to more closely correspond to the actual image of the body of the user, as in 1012. Personalized 3D body model refinement is discussed above and discussed further below with respect to FIGS. 11A and 11B.

As discussed below, the personalized 3D body model refinement process 1100 (FIG. 11A) returns a refined silhouette, as in 1014. Upon receipt of the refined silhouette, the example process 1000 again generates body parameters, as in 1008, and continues. This may be done until no further refinements are to be made to the silhouette. In comparison, the personalized 3D body model refinement process 1150 (FIG. 11B) generates and returns a refined personalized 3D body model and the example process 1000 continues at block 1016.

Figure 11A:
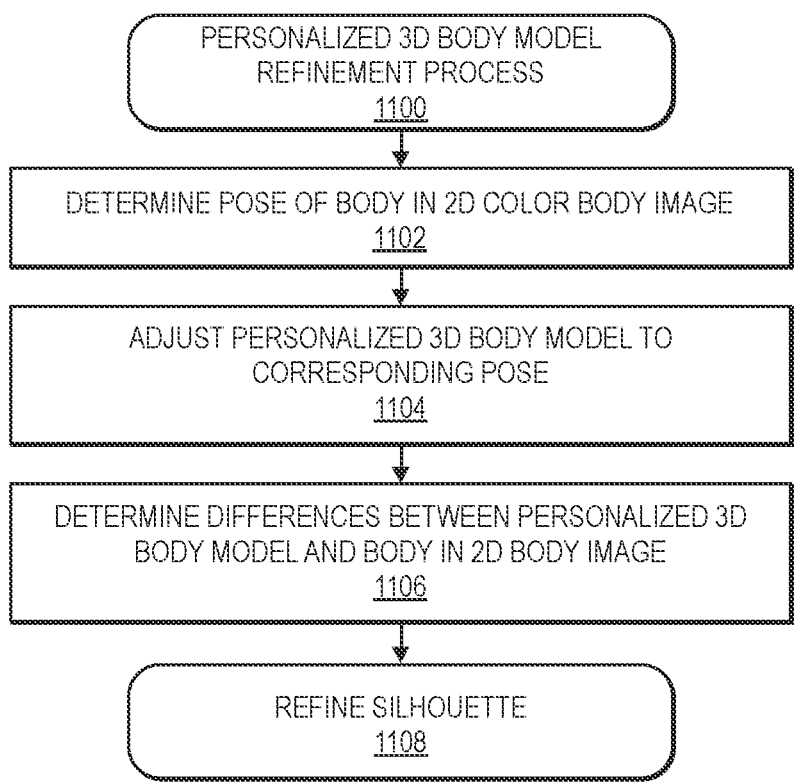
FIG. 11A is an example flow diagram of a three-dimensional body model refinement process, in accordance with implementations of the present disclosure.
Figure 11B:
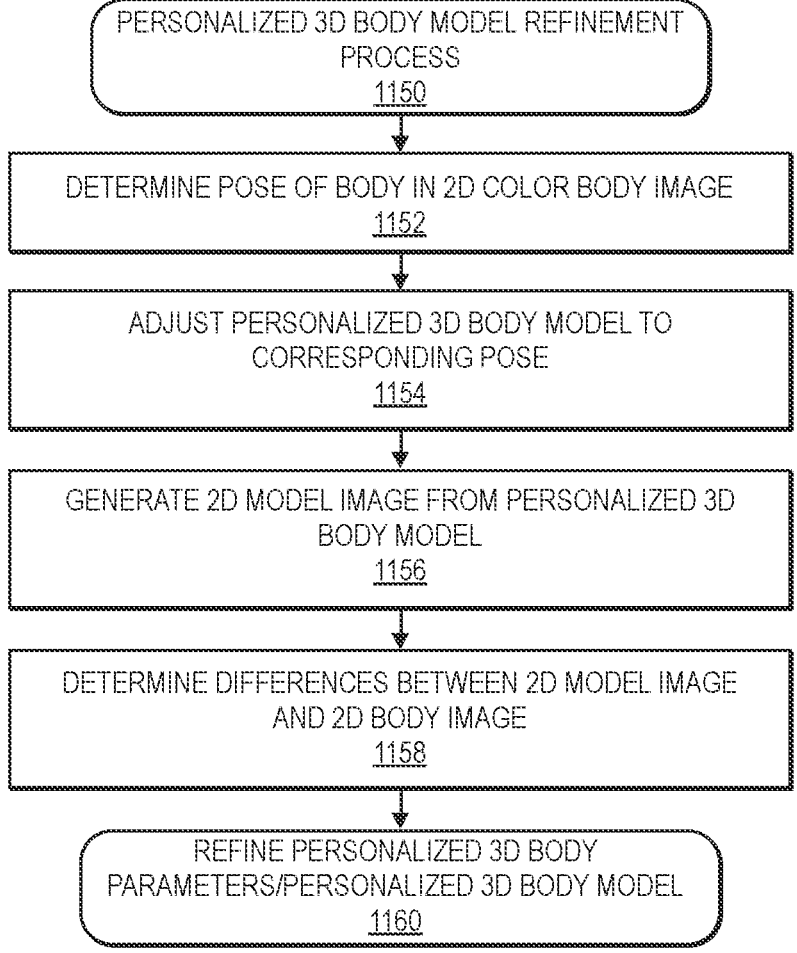
FIG. 11B is another example flow diagram of a three-dimensional body model refinement process, in accordance with implementations of the present disclosure.

After refinement of the silhouette and generation of a personalized 3D body model from refined body parameters, or after receipt of the refined personalized 3D body model from FIG. 11B, one or more textures (e.g., skin tone, hair, clothing, etc.) from the 2D color body images may be applied to the personalized 3D body model, as in 1016. Finally, the personalized 3D body model may be provided to the user as representative of the body of the user and/or other personalized 3D body model information (e.g., body mass, joint locations, arm length, body fat percentage, etc.) may be determined from the model, as in 1018.

FIG. 11A is an example flow diagram of a personalized 3D body model refinement process 1100, in accordance with implementations of the present disclosure. The example process 1100 begins by determining a pose of a body represented in one of the 2D color body images, as in 1102. A variety of techniques may be used to determine the approximate pose of the body represented in a 2D color body image. For example, camera parameters (e.g., camera type, focal length, shutter speed, aperture, etc.) included in the metadata of the 2D color body image may be obtained and/or additional camera parameters may be determined and used to estimate the approximate pose of the body represented in the 2D color body image. For example, a personalized 3D body model may be used to approximate the pose of the body in the 2D color body image and then a position of a virtual camera with respect to that model that would produce the 2D color body image of the body may be determined. Based on the determined position of the virtual camera, the height and angle of the camera used to generate the 2D color body image may be inferred. In some implementations, the camera tilt may be included in the metadata and/or provided by a portable device that includes the camera. For example, many portable devices include an accelerometer and information from the accelerometer at the time the 2D color body image was generated may be provided as the tilt of the camera. Based on the received and/or determined camera parameters, the pose of the body represented in the 2D color body image with respect to the camera may be determined, as in 1102.

The personalized 3D body model of the body of the user may then be adjusted to correspond to the determined pose of the body in the 2D color body image, as in 1104. With the personalized 3D body model adjusted to approximately the same pose as the user represented in the image, the shape of the personalized 3D body model may be compared to the shape of the body in the 2D color body image and/or the silhouette to determine any differences between the personalized 3D body model and the representation of the body in the 2D color body image and/or silhouette, as in 1106.

In some implementations, it may be determined whether any determined difference is above a minimum threshold (e.g., 2%). If it is determined that there is a difference between the personalized 3D body model and the body represented in one or more of the 2D color body images, the silhouette may be refined, as in 1108. The silhouette may then be used to generate refined body parameters for the body represented in the 2D color body images, as discussed above with respect to FIG. 10. If the silhouette is refined, the refined silhouette is returned to the example process 1000, as discussed above and as illustrated in block 1014 (FIG. 10). If no difference is determined or if it is determined that the difference does not exceed a minimum threshold, an indication may be returned to the example process 1000 that there are no differences between the personalized 3D body model and the 2D color body image/silhouette.

FIG. 11B is an example flow diagram of another personalized 3D body model refinement process 1150, in accordance with implementations of the present disclosure. The example process 1150 begins by determining a pose of a body represented in one of the 2D color body images, as in 1152. A variety of techniques may be used to determine the approximate pose of the body represented in a 2D color body image. For example, camera parameters (e.g., camera type, focal length, shutter speed, aperture, etc.) included in the metadata of the 2D color body image may be obtained and/or additional camera parameters may be determined and used to estimate the approximate pose of the body represented in the 2D color body image. For example, a personalized 3D body model may be used to approximate the pose of the body in the 2D color body image and then a position of a virtual camera with respect to that model that would produce the 2D color body image of the body may be determined. Based on the determined position of the virtual camera, the height and angle of the camera used to generate the 2D color body image may be inferred. In some implementations, the camera tilt may be included in the metadata and/or provided by a portable device that includes the camera. For example, many portable devices include an accelerometer and information from the accelerometer at the time the 2D color body image was generated may be provided as the tilt of the camera. Based on the received and/or determined camera parameters, the pose of the body represented in the 2D color body image with respect to the camera may be determined, as in 1152.

The personalized 3D body model of the body of the user may then be adjusted to correspond to the determined pose of the body in the 2D color body image, as in 1154. With the personalized 3D body model adjusted to approximately the same pose as the user represented in the image, a 2D model image from the personalized 3D body model is generated, as in 1156. The 2D model image may be generated, for example, by converting or imaging the personalized 3D body model into a 2D image with the determined pose, as if a digital 2D image of the personalized 3D body model had been generated. Likewise, the 2D model image may be a binary image with pixels corresponding to the model having a first set of values (e.g., white—RGB values of 255, 255, 255) and pixels that do not represent the model having a second set of values (e.g., black—RGB values of 0), 0, 0)

The 2D model image is then compared with the 2D color body image and/or the silhouette to determine any differences between the 2D model image and the representation of the body in the 2D color body image and/or silhouette, as in 1158. For example, the 2D model image may be aligned with the 2D color body image and/or the silhouette and pixels between the images compared to determine differences between the pixel values. In implementations in which the pixels are binary (e.g., white or black) an error (e.g., % difference) may be determined as a difference in pixel values between the 2D model image and the 2D color body image. That error is differentiable and may be utilized to adjust the body parameters and, as a result, the shape of the personalized 3D body model.

In some implementations, it may be determined whether any determined difference is above a minimum threshold (e.g., 2%). If it is determined that there is a difference between the 2D model image and the body represented in one or more of the 2D color body images/silhouette, the personalized 3D body model and/or the body parameters may be refined to correspond to the shape and/or size of body represented in the 2D color body image and/or the silhouette, as in 1160. This example process 1150 may continue until there is no difference between the 2D model image and the 2D color body image/silhouette, or the difference is below a minimum threshold. As discussed above, the refined personalized 3D body model produced from the example process 1150, or if no refinements are necessary, the personalized 3D body model is returned to example process 1000 at block 1012 and the process 1000 continues.

FIG. 12 is an example image based regional body composition generation processes 1200, in accordance with disclosed implementations.

The example process 1200 begins upon receipt of one or more 2D color body images of a body, as in 1202. As noted above, the disclosed implementations are operable with any number of 2D color body images for use in generating body dimensions of the body represented in the image. For example, in some implementations, a single 2D color body image may be used. In other implementations, two, three, four, or more 2D color body images may be used.

As discussed above, the 2D color body images may be generated using any 2D imaging element, such as a camera on a portable device, a webcam, etc. The received 2D color body images are then segmented to produce a binary silhouette of the body represented in the one or more 2D color body images, as in 1204. As discussed above, one or more segmentation techniques, such as background subtraction, semantic segmentation, Canny edge detectors or algorithms, Sobel operators, algorithms or filters, Kayyali operators, Roberts edge detection algorithms, Prewitt operators, Frei-Chen methods, or any other algorithms or techniques that may be known to those of ordinary skill in the pertinent arts. In some implementations, the silhouette may be further segmented into body segments.

In addition, in some implementations, the silhouette(s) may be normalized in height and centered in the image before further processing, as in 1206. For example, the silhouettes may be normalized to a standard height based on a function of a known or provided height of the body of the user represented in the image and an average height (e.g., average height of female body, average height of male body). In some implementations, the average height may be more specific than just gender. For example, the average height may be the average height of a gender and a race corresponding to the body, or a gender and a location (e.g., United States) of the user, etc.

The silhouette(s) of the body represented in the 2D image(s) may then be further processed to determine personalized body features of the body, as discussed above, as in 1207. As discussed above, in some implementations the one or more 2D images may be processed to determine body features of the body represented in the image. Those body features of the different 2D color body images may then be concatenated to generate personalized body features. In addition, in some implementations, the personalized body features may be refined based on feedback from 3D body model generation, as discussed herein. In some implementations, the silhouette(s) may be sent directly to the trained body dimension model for processing. In other implementations, as discussed above, the silhouettes, if there are more than one, may be concatenated and/or further processed to generate personalized body features representative of the body and corresponding silhouette. The personalized body features determined from the silhouette(s) may then be provided to the trained regional body composition model and the regional body composition model may generate image based regional body composition values for the body represented in the 2D image(s) based on the received personalized body features, as in 1208.

Finally, the image based regional body composition values determined by the trained regional body composition model may be provided, as in 1210. In some implementations, the determined regional body composition values may be included in a presentation along with a generated personalized 3D body model of the body, with other body dimensions, etc. In other examples, the regional body composition values may be used to group or classify the body into a cohort and/or to provide information regarding the regional body composition values determined for the body compared to regional body composition values of others in the same cohort, having a similar age, gender, etc.

Figure 13:
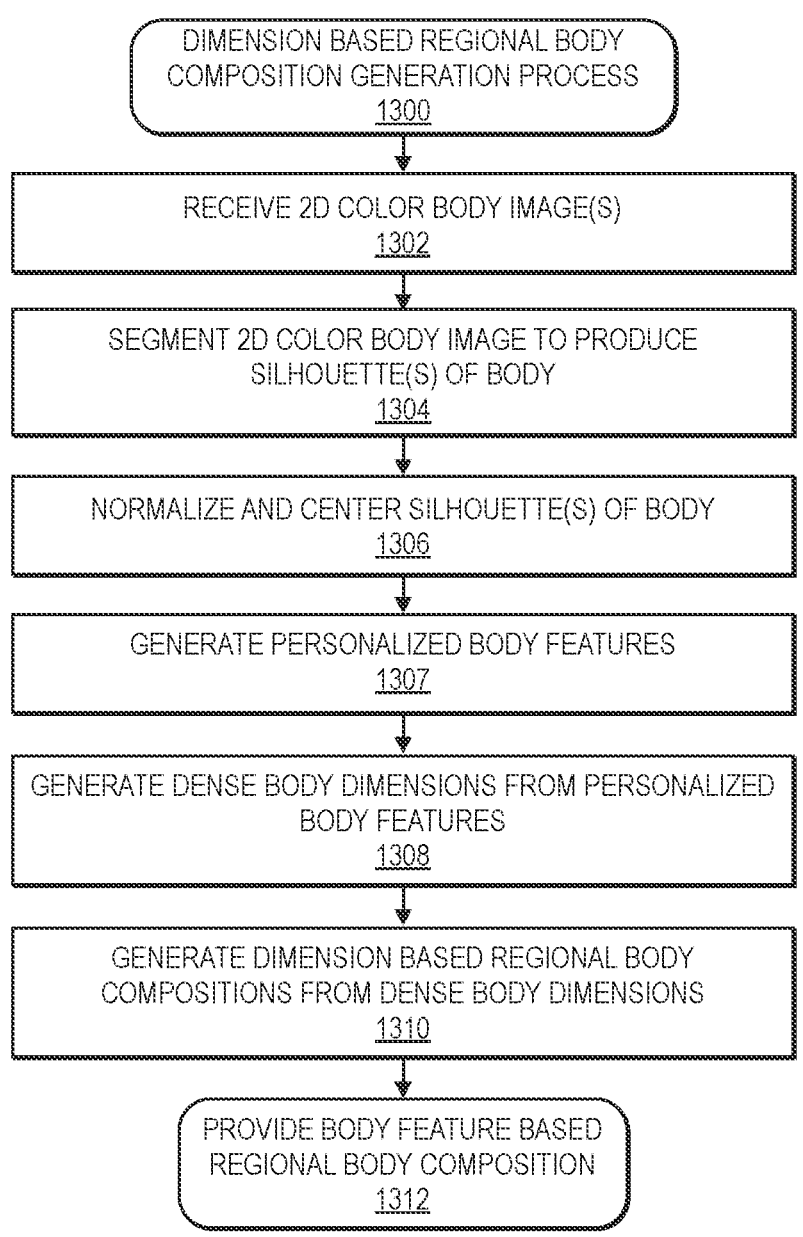
FIG. 13 is an example dimension based regional body composition generation process, in accordance with implementations of the present disclosure.

FIG. 13 is an example dimension based regional body composition generation process 1300, in accordance with implementations of the present disclosure.

The example process 1300 begins upon receipt of one or more 2D color body images of a body, as in 1302. As noted above, the disclosed implementations are operable with any number of 2D color body images for use in generating body dimensions of the body represented in the image. For example, in some implementations, a single 2D color body image may be used. In other implementations, two, three, four, or more 2D color body images may be used.

As discussed above, the 2D color body images may be generated using any 2D imaging element, such as a camera on a portable device, a webcam, etc. The received 2D color body images are then segmented to produce a binary silhouette of the body represented in the one or more 2D color body images, as in 1304. As discussed above, one or more segmentation techniques, such as background subtraction, semantic segmentation, Canny edge detectors or algorithms, Sobel operators, algorithms or filters, Kayyali operators, Roberts edge detection algorithms, Prewitt operators, Frei-Chen methods, or any other algorithms or techniques that may be known to those of ordinary skill in the pertinent arts. In some implementations, the silhouette may be further segmented into body segments.

In addition, in some implementations, the silhouette(s) may be normalized in height and centered in the image before further processing, as in 1306. For example, the silhouettes may be normalized to a standard height based on a function of a known or provided height of the body of the user represented in the image and an average height (e.g., average height of female body, average height of male body). In some implementations, the average height may be more specific than just gender. For example, the average height may be the average height of a gender and a race corresponding to the body, or a gender and a location (e.g., United States) of the user, etc.

The silhouette(s) of the body represented in the 2D image(s) may then be further processed to determine personalized body features of the body, as discussed above, as in 1307. As discussed above, in some implementations the one or more 2D images may be processed to determine body features of the body represented in the image. Those body features of the different 2D color body images may then be concatenated to generate personalized body features. In addition, in some implementations, the personalized body features may be refined based on feedback from 3D body model generation, as discussed herein. In some implementations, the silhouette(s) may be sent directly to the trained body dimension model for processing. In other implementations, as discussed above, the silhouettes, if there are more than one, may be concatenated and/or further processed to generate personalized body features representative of the body and corresponding silhouette.

The personalized body features determined from the silhouette(s) may then be utilized to generate dense body dimensions for the body represented in the 2D image, as in 1308. For example, a body dimensions model, such as the body dimension CNN discussed above, may be trained to determine regional body dimensions, such as bicep circumferences, thigh circumferences, etc., for different regions of the body represented in the one or more 2D images. The regional body dimensions may be included in the dense body dimensions. As discussed above, utilizing the dense body dimensions, a dimension based regional body composition model may be used to generate dimension based regional body composition values for different regions of the body, as in 1310.

Finally, the dimensions based regional body composition values determined by the trained regional body composition model may be provided, as in 1312. In some implementations, the determined regional body composition values may be included in a presentation along with a generated personalized 3D body model of the body, with other body dimensions, etc. In other examples, the dimension based regional body composition values may be used to group or classify the body into a cohort and/or to provide information regarding the dimension based regional body composition values determined for the body compared to dimension based regional body composition values of others in the same cohort, having a similar age, gender, etc.

FIG. 14 is an example fusion based regional body composition generation process 1400, in accordance with implementations of the present disclosure. As discussed above, the fusion based regional body composition values may be generated based on both the image based regional body composition values determined from the example image based regional body composition generation process 1200 (FIG. 12) and the dimension based regional body composition values determined from the example dimension based regional body composition generation process 1300 (FIG. 13).

The example process 1400 begins by receiving the image based regional body composition values for a body as determined by the example image based regional body composition process 1200 discussed with respect to FIG. 12, as in 1402, and the dimension based regional body composition values for the body as determined by the example dimension based regional body composition process 1300 discussed with respect to FIG. 13, as in 1404.

In addition, in some implementations, a weighting between the image based regional body composition values and the dimension based regional body composition values may be determined, as in 1406. For example, in some implementations, the results of the image based regional body composition process 1200 may provide better or more accurate results than the dimension based regional composition process 1300. For example, if the user is wearing minimal tight-fitting clothing, the image based regional body composition process 1200 may provide more accurate results than the dimension based regional body composition process and therefore receive a higher weighting for the example process 1300. In other examples, if the user is wearing looser clothing, the dimension based regional body composition model may provide more accurate results and be assigned a higher weighting for the example process 1300.

In one example, one or more of the 2D color body images may be processed to determine the clothing or attire, and/or other attributes of the body represented in the 2D images, and a weighting assigned accordingly. In other examples, a confidence value may be output by each of the image based regional body composition model and the dimension based regional body composition model indicating a confidence in the accuracy of the respective image based regional body composition values and dimension based regional body composition values output. Based on the image processing, confidence values, and/or other indicators, a weighting may be applied by the example process 1400 to weight one of the regional body composition values higher than the other. In other examples, no weighting may be applied.

The image based regional body composition values and the dimension based regional body composition values may then be combined according to the determined weighting to produce fusion based regional body composition values, as in 1408. For example, a weighted average may be determined between the two values to produce the fusion based regional body composition values. As will be appreciated, the example process and the fusion based regional body composition values may be determined for each regional body composition value generated for each of the different regions of a body.

Finally, the determined fusion based regional body composition values may be provided, as in 1410. In some implementations, the determined fusion based regional body composition values may be included in a presentation along with a generated personalized 3D body model of the body, with other body dimensions, etc. In other examples, the fusion based regional body composition values may be used to group or classify the body into a cohort and/or to provide information regarding the fusion based regional body composition values determined for the body compared to regional body composition values of others in the same cohort, having a similar age, gender, etc.

Although the disclosure has been described herein using exemplary techniques, components, and/or processes for implementing the systems and methods of the present disclosure, it should be understood by those skilled in the art that other techniques, components, and/or processes or other combinations and sequences of the techniques, components, and/or processes described herein may be used or performed that achieve the same function(s) and/or result(s) described herein and which are included within the scope of the present disclosure.

Additionally, in accordance with the present disclosure, the training of machine learning tools (e.g., artificial neural networks or other classifiers) and the use of the trained machine learning tools to detect body pose, determine body point locations, determine body direction, determine body dimensions of the body, determine regional body composition values for regions of the body, and/or to generate personalized 3D body models of a body based on one or more 2D color body images of that body may occur on multiple, distributed computing devices, or on a single computing device, as described herein.

Likewise, while the above discussions focus primarily on a personalized 3D body model, body dimensions, and/or regional body composition values for regions of the body being generated from multiple 2D body direction images, in some implementations, the personalized 3D body model, body dimensions, and/or regional body composition values may be generated based on a single 2D body direction image of the body. In other implementations, two or more 2D body direction images may be used with the disclosed implementations.

Still further, while the above implementations are described with respect to generating personalized 3D body models, body dimensions, and/or regional body composition values of human bodies represented in 2D color body images, in other implementations, non-human bodies, such as dogs, cats, or other animals may be modeled in 3D, body dimensions, and/or regional body composition values determined based on 2D images of those bodies. Accordingly, the use of a human body in the disclosed implementations should not be considered limiting.

It should be understood that, unless otherwise explicitly or implicitly indicated herein, any of the features, characteristics, alternatives or modifications described regarding a particular implementation herein may also be applied, used, or incorporated with any other implementation described herein, and that the drawings and detailed description of the present disclosure are intended to cover all modifications, equivalents and alternatives to the various implementations as defined by the appended claims. Moreover, with respect to the one or more methods or processes of the present disclosure described herein, including but not limited to the flow charts illustrated and discussed herein, orders in which such methods or processes are presented are not intended to be construed as any limitation on the claimed inventions, and any number of the method or process steps or boxes described herein can be combined in any order and/or in parallel to implement the methods or processes described herein. Likewise, in some implementations, one or more steps or orders of the methods or processes may be omitted. Also, the drawings herein are not drawn to scale.

Conditional language, such as, among others, "can," "could," "might," or "may," unless specifically stated otherwise, or otherwise understood within the context as used, is generally intended to convey in a permissive manner that certain implementations could include, or have the potential to include, but do not mandate or require, certain features, elements and/or steps. In a similar manner, terms such as "include," "including" and "includes" are generally intended to mean "including, but not limited to." Thus, such conditional language is not generally intended to imply that features, elements and/or steps are in any way required for one or more implementations or that one or more implementations necessarily include logic for deciding, with or without user input or prompting, whether these features, elements and/or steps are included or are to be performed in any particular implementation.

Disjunctive language such as the phrase "at least one of X, Y, or Z," or "at least one of X, Y and Z," unless specifically stated otherwise, is otherwise understood with the context as used in general to present that an item, term, etc., may be either X, Y, or Z, or any combination thereof (e.g., X, Y, and/or Z). Thus, such disjunctive language is not generally intended to, and should not, imply that certain implementations require at least one of X, at least one of Y, or at least one of Z to each be present.

Unless otherwise explicitly stated, articles such as "a" or "an" should generally be interpreted to include one or more described items. Accordingly, phrases such as "a device configured to" are intended to include one or more recited devices. Such one or more recited devices can also be collectively configured to carry out the stated recitations. For example, "a processor configured to carry out recitations A, B and C" can include a first processor configured to carry out recitation A working in conjunction with a second processor configured to carry out recitations B and C.

Language of degree used herein, such as the terms "about," "approximately," "generally," "nearly" or "substantially" as used herein, represent a value, amount, or characteristic close to the stated value, amount, or characteristic that still performs a desired function or achieves a desired result. For example, the terms "about," "approximately," "generally," "nearly" or "substantially" may refer to an amount that is within less than 10% of, within less than 5% of, within less than 1% of, within less than 0.1% of, and within less than 0.01% of the stated amount.

Although the invention has been described and illustrated with respect to illustrative implementations thereof, the foregoing and various other additions and omissions may be made therein and thereto without departing from the spirit and scope of the present disclosure.

What is claimed is:

1. A computer-implemented method, comprising:

processing a two-dimensional ("2D") color body image of a human body to determine a plurality of dimension based regional body composition values for at least one region of the human body;

processing the 2D color body image to determine a plurality of image based regional body composition values for the at least one region of the human body;

combining the plurality of dimension based regional body composition values and the plurality of image based regional body composition values to determine a plurality of regional body composition values for the at least one region; and causing a presentation of at least some of the plurality of regional body composition values determined for the at least one region of the human body.

2. The computer-implemented method of claim 1, wherein the at least one region includes at least one of a left arm, a right arm, a left leg, a right leg, a full body, a right bicep, a right forearm, a right upper leg, a right lower leg, a trunk, an android, or a gynoid.

3. The computer-implemented method of claim 1, wherein determining the plurality of regional body composition values includes:

processing the 2D color body image to segment a first plurality of pixels of the 2D color body image that represent the human body from a second plurality of pixels of the 2D color body image that do not represent the human body to produce a silhouette of the human body; and processing the silhouette to produce the plurality of regional body composition values.

4. The computer-implemented method of claim 1, wherein:

processing the 2D color body image to determine the plurality of image based regional body composition values, further includes:

processing the 2D color body image to determine a plurality of personalized body features corresponding to the human body represented in the 2D color body image; and processing the plurality of personalized body features with a first neural network to determine the plurality of image based regional body composition values; and processing the 2D color body image to determine the plurality of dimension based regional body composition values, further includes:

processing the plurality of personalized body features with a second neural network to determine a plurality of body dimensions of the human body; and processing the plurality of body dimensions with a third neural network to determine the plurality of dimension based regional body composition values.

5. The computer-implemented method of claim 1, wherein the plurality of regional body composition values include at least one of a fat tissue mass for the region, a lean tissue mass for the region, or a bone mineral density for the region.

6. A computing system, comprising:

one or more processors;

a memory storing program instructions that, when executed by the one or more processors, cause the one or more processors to at least:

receive at least one two-dimensional ("2D") color body image of a body, wherein:

each of the at least one 2D color body image is generated by a 2D imaging element; and each of the at least one 2D color body image includes a representation of the body from a different view; and process, using a neural network, each of the at least one 2D color body image to, at least:

determine a plurality of dimension based regional body composition values for a region of the body:

determine a plurality of image based regional body composition values for the region; and combine the plurality of dimension based regional body composition values and the plurality of image based regional body composition values to determine a plurality of regional body composition values for the region.

7. The computing system of claim 6, wherein the region of the body includes at least one of a full body region, a left arm region, a right arm region, a left leg region, a right leg region, a trunk region, an android region, or a gynoid region.

8. The computing system of claim 6, wherein the program instructions that, when executed by the one or more processors to determine the plurality of image based regional body composition values, further include instructions that cause the one or more processors to at least:

process the at least one 2D color body image to determine a plurality of personalized body features corresponding to the body; and process the plurality of personalized body features to determine the plurality of image based regional body composition values.

9. The computing system of claim 6, wherein the program instructions that, when executed by the one or more processors to determine the plurality of dimension based regional body composition values, further include instructions that cause the one or more processors to at least:

process the at least one 2D color body image to determine a plurality of body dimensions corresponding to the body; and process the plurality of body dimensions to determine the plurality of dimension based regional body composition values.

10. The computing system of claim 6, wherein;

the program instructions that, when executed by the one or more processors to determine the plurality of image based regional body composition values, further include instructions that cause the one or more processors to at least:

process the at least one 2D color body image to determine personalized body features corresponding to the body; and process the personalized body features to determine the plurality of image based regional body composition values;

the program instructions that, when executed by the one or more processors to determine the plurality of image based regional body composition values, further include instructions that cause the one or more processors to at least:

process the at least one 2D color body image to determine a plurality of body dimensions corresponding to the body; and process the plurality of body dimensions to determine the plurality of dimension based regional body composition values; and combine the plurality of image based regional body composition values and the plurality of dimension based regional body composition values to produce the plurality of regional body composition values.

11. The computing system of claim 6, wherein the program instructions that, when executed by the one or more processors to determine the plurality of regional body composition values, further include instructions that cause the one or more processors to at least:

determine a weighting to apply to at least one of the plurality of image based regional body composition values or the plurality of dimension based regional body composition values; and combine the plurality of image based regional body composition values and the plurality of dimension based regional body composition values based at least in part on the weighting.

12. The computing system of claim 6, wherein the program instructions that, when executed by the one or more processors to process each of the at least one 2D color body image, further include instructions that cause the one or more processors to at least:

combine, using the neural network, each of the plurality of dimension based regional body composition values, the plurality of image based regional body composition values and at least one body trait of the body to determine the plurality of regional body composition values.

13. The computing system of claim 12, wherein the at least one body trait is at least one of a height of the body, a weight of the body, an age, an ethnicity, or a gender of the body.

14. The computing system of claim 6, wherein the program instructions that, when executed by the one or more processors to cause the one or more processors to process each of the at least one 2D color body image, further include instructions that, when executed by the one or more processors, further cause the one or more processors to at least:

process a first 2D color body image of the at least one 2D color body image to produce a first plurality of features representative of the body; and process a second 2D color body image of the at least one 2D color body image to produce a second plurality of features representative of the body.

15. The computing system of claim 14, wherein the program instructions that, when executed by the one or more processors to cause the one or more processors to process each of the at least one 2D color body image, further include instructions that, when executed by the one or more processors, further cause the one or more processors to at least:

concatenate the first plurality of features and the second plurality of features to produce concatenated features; and process the concatenated features to produce the plurality of regional body composition values.

16. The computing system of claim 6, wherein the program instructions that, when executed by the one or more processors, further cause the one or more processors to at least:

process, using a second neural network, each of the at least one 2D color body image to determine a three-dimensional model representative of the body; and send, for presentation, the three-dimensional model and at least one of the plurality of regional body composition values.

17. A method, comprising:

determining at least one region of a body represented in a two-dimensional ("2D") color body image, wherein the at least one region is less than all of the body;

processing the 2D color body image to determine a plurality of dimension based regional body composition values for the region;

processing the 2D color body image to determine a plurality of image based regional body composition values for the region; and combining the plurality of dimension based regional body composition values and the plurality of image based regional body composition values to determine a plurality of regional body composition values corresponding to the at least one region; and sending for presentation the plurality of regional body composition values corresponding to the at least one region.

18. The method of claim 17, further comprising:

generating a three-dimensional ("3D") model of the body; and wherein sending includes sending for presentation the 3D model of the body and the plurality of regional body composition values.

19. The method of claim 17, wherein the plurality of regional body composition values include at least two of a left arm region, a right arm region, a left leg region, a right leg region, a trunk region, an android region, or a gynoid region.

20. The method of claim 17, wherein combining includes:

combining the plurality of dimension based regional body composition values, the plurality of image based regional body composition values, and at least one trait about the body to determine the plurality of regional body composition values.

* * * * *